(12) United States Patent
Hain et al.

(10) Patent No.: US 7,208,318 B2
(45) Date of Patent: Apr. 24, 2007

(54) METHOD FOR PRODUCING PLANTS WITH SUPPRESSED PHOTORESPIRATION AND IMPROVED CO₂ FIXATION

(75) Inventors: Rudiger Hain, Frankfurt (DE); Dieter Berg, Langenfeld (DE); Christoph Peterhansel, Aachen (DE); Fritz Kreuzaler, Aachen (DE); Rafijul Bari, Memphis, TN (US); Dagmar Weier, Aachen (DE); Heinz-Josef Hirsch, Aachen (DE); Thomas Rademacher, Aachen (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 10/515,716

(22) PCT Filed: May 23, 2003

(86) PCT No.: PCT/EP03/05398

§ 371 (c)(1),
(2), (4) Date: Aug. 12, 2005

(87) PCT Pub. No.: WO03/100066

PCT Pub. Date: Dec. 4, 2003

(65) Prior Publication Data

US 2006/0095981 A1 May 4, 2006

(30) Foreign Application Priority Data

May 27, 2002 (EP) ................................. 02011578

(51) Int. Cl.
*A01H 5/00* (2006.01)
*C12N 15/82* (2006.01)
*C12N 15/87* (2006.01)
*C12N 5/14* (2006.01)
*C07H 21/00* (2006.01)

(52) U.S. Cl. .................... 435/468; 435/320.1; 435/419; 536/23.6; 800/278; 800/288

(58) Field of Classification Search .................... None
See application file for complete search history.

(56) References Cited

U.S. PATENT DOCUMENTS 6,610,913 B1 8/2003 Arai et al.

FOREIGN PATENT DOCUMENTS

EP          0874056 A1      10/1998
WO          WO98/35030       8/1998

OTHER PUBLICATIONS

Yamaguchi et al., Plant Cell Physiol., 41:1397-1406, 2000.*
Parry et al. (ASPB Meeting, Aug. 2002, Abstract # 603).*
Dounce et al. (Current Opinion in Plant Biology, 2:214-222, 1999).*
Guo Zh, Zhang JW and Wang HN (2005) GenBank Accession No. DQ141598, Zea mays cultivar Nongda 105 polyubiquitin-1 (Ubi-1) gene, promoter region and 5' UTR, 1992 bp DNA.
Cornah JE, Germain V, Ward JL, Beale MH, Smith SM (2004) Lipid utilization, gluconeogenesis, and seedling growth in Arabidopsis mutants lacking the glyoxylate cycle enzyme malate synthase, J Biol Chem. 279:42916-23.
Carozzi NB, Rabe SM, Miles PJ, Warren GW and de Haan PT (2002) GenBank Accession No. AX392813 (GI:19700915), Sequence 16 from Patent WO0215701, 14603 bp DNA. Maize ubiquitin promoter: bp 11142-12032.
Beaujean A, Issakidis-Bourguet E, Catterou M, Dubois F, Sangwan R and Sangwan-Norreel B (2001) Integration and expression of Sorghum C-4 phosphoenolpyruvate carboxylase and chloroplastic NADP(+)-malate dehydrogenase separately or together in C-3 potato plants. Plant Science 160: 1199-1210.
Bock R (2001) Transgenic plastids in basic research and plant biotechnology. J Mol Biol 312: 425-438.
Hausler RE, Rademacher T, Li J, Lipka V, Fischer KL, Schubert S, Kreuzaler F, Hirsch HJ (2001) Single and double overexpression of C(4)-cycle genes had differential effects on the pattern of endogenous enzymes, attenuation of photorespiration and on contents of UV protectants in transgenic potato and tobacco plants. Exp Bot. 52(362):1785-803.
Matsuoka M, Furbank RT, Fukayama H and Miyao M (2001) Molecular engineering of C₄ photosynthesis. Annu Rev Plant Physio. Plant Mol Biol 52: 297-314.
Rademacher TR (2001), GenBank Accession No. AY027531, Binary vector pPAM, complete sequence, 3098 bp DNA.
Suzuki S, Murai N, Burnell James N and Arai M (2000) Changes in photosynthetic carbon flow in transgenic rice plants that express C4-type phosphoenolpyruvate carboxykinase from *Urochloa panicoides*. Plant Physiology 124: 163-172.

(Continued)

*Primary Examiner*—Ashwin Mehta
*Assistant Examiner*—Vinod Kumar
(74) *Attorney, Agent, or Firm*—Baker Botts LLP

(57) ABSTRACT

The invention relates to a method for the production of plants with suppressed photo-respiration and improved CO₂ fixation. In particular, the invention relates to a re-use of phosphoglycolate produced in photorespiration. The reaction product will be converted to a component that may be reintegrated into the plant assimilatory metabolism inside the chloroplast. This is accomplished by the transfer of genes derived from glycolate-utilizing pathways from bacteria, algae, plants and/or animals including humans into the plant nuclear and/or plastidial genome. The method of the invention leads to a reduction of photorespiration in C₃ plants and by this will be of great benefit for food production especially but not exclusively under non-favourable growth conditions.

29 Claims, 9 Drawing Sheets

OTHER PUBLICATIONS

Cushman JC and Bohnert HJ (1999) Crassulacean acid metabolism : molecular genetics. Annu Rev Plant Physiol Plant Mol Biol 50: 305-332.

Kanai R and Edwards GE (1999). The Biochemistry of $C_4$ Photosynthesis. In $C_4$ Plant Biology, R.K. Monson, ed (San Diego: Academic Press), pp. 49-87.

Ku MS, Agarie S, Nomura M, Fukayama H, Tsuchida H, Ono K, Hirose S, Toki S, Miyao M and Matsuoka M (1999) High-level expression of maize phosphoenolpyruvate carboxylase in transgenic rice plants. Nat Biotechnol 17: 76-80.

Lipka V, Hausler RE, Rademacher T, Li J, Hirsch HJ and Kreuzaler F (1999) *Solanum tuberosum* double transgenic expressing phosphoenolpyruvate carboxylase and NADP-malic enzyme display reduced electron requirement for CO2 fixation. Plant Science. 144: 93-105.

Rumsby G and Cregeen DP (1999) Identification and expression of a cDNA for human hydroxypyruvate/glyoxylate reductase. Biochimica et Biophysica Acta 1446: 383-388.

Arp WJ, Van Mierlo JEM, Berendse F and Snijders W (1998) Interactions between elevated CO2 concentration, nitrogen and water: Effects on growth and water use of six perennial plant species. Plant, Cell & Environment 21: 1-11.

Hall GE Jr. and Spiker S (1998) GenBank Accession No. U67919, Nicotiana tabacum Rb7 matrix attachment regions/scaffold attachment region sequence, 1168 bp DNA.

Reiskind JB, Madsen TV, Van Ginkel LC and Bowes G (1997) Evidence that inducible $C_4$-type photosynthesis is a chloroplastic $CO_2$-concentrating mechanism in *Hydrilla*, a submersed monocot. Plant Cell Environ 20: 211-220.

Tolbert NE (1997) The $CO_2$ oxidative photosynthetic carbon cycle. Annu Rev Plant Physiol Plant Mol Biol 48: 1-25.

Gehlen J, Panstruga R, Smets H, Merkelbach S, Kleines M, Porsch P, Fladung M, Becker I, Rademacher T, Hausler RE and Hirsch HJ (1996) Effects of altered phosphoenolpyruvate carboxylasse activities on transgenic C3 plant Solanum tuberosum. Plant Molecular Biology 32: 831-848.

Pellicer MT, Badia J, Aguilar J and Baldoma L (1996) glc locus of *Escherichia coli*: characterizatFion of genes encoding the subunits of glycolate oxidase and the glc regulator protein. Journal of Bacteriology 178: 2051-2059.

Reichel C, Mathur J, Eckes P, Langenkemper K, Koncz C, Schell J, Reiss B and Maas C (1996) Enhanced green fluorescence by the expression of an Aequorea victoria green fluorescent protein mutant in mono- and dicotyledonous plant cells. Proc. National Academy of Sciences USA 93: 5888-5893.

Staneloni RJ (1996) GenBank Accession No. U56861 (GI: 1890636), *Nicotiana plumbaginifolia* intergenic region between lhcb1*1 and lhcbl*2 genes, 1705 bp DNA.

Leegood RC, Lea PJ, Adcock MD and Haeusler RE (1995) The regulation and control of photorespiration. Journal of Experimental Botany 46: 1397-1414.

Kogami H, Shono M, Koike T, Yanagisawa S, Izui K, Sentoku N, Tanifuji S, Uchimiya H and Toki S (1994) Molecular and physiological evaluation of transgenic tobacco plants expressing a maize phosphoenolpyruvate carboxylase gene under the control of the cauliflower mosaic virus 35S promoter. Transgenic Research 3: 287-296.

Chang YY, Wang AY and Cronan JE, Jr. (1993) Molecular cloning, DNA sequencing, and biochemical analyses of *Escherichia coli* glyoxylate carboligase. An enzyme of the acetohydroxy acid synthase-pyruvate oxidase family. Journal of Biological Chemistry 268: 3911-3919.

Hudspeth RL, Grula JW, Dai Z, Edwards GE and Ku MSB (1992) Expression of maize phosphoenolpyruvate carboxylase in transgenic tobacco. Plant Physiol 98: 458-464.

Manzara T. (1992), Genbannk Accession No. X66070 (GI: 22624), L.esculentum rbcS3 A gene for Rubisco LSU8, 567 bp DNA.

Ramazanov Z and Cardenas J (1992) Involvement of photorespiration and glycolate pathway in carbonic anhydrase induction and inorganic carbon concentration in *Chlamydomonas reinhardtii*. Physiologia Plantarum 84: 502-508.

Schreier PH (1992) GenBank Accession No. X69763, S.tuberosum rbxS3 gene for ribulose-(1,5)-bisphosphate carboxylase/oxygenase small subunit, 1598 bp DNA.

Schreier PH (1992) GenBank Accession No. X69762, S.tubersum rbcS2c gene for ribulose-(1,5)-biphosphate carboxylase/oxygenase small subunit, 1386 bp DNA.

Schreier PH (1992) GenBank Accession No. X69761, S.tubersum rbcS2b gene for ribulose-(1,5)-biphosphate carboxylase/oxygenase small subunit, 1703 bp DNA.

Schreier PH (1992) GenBank Accession No. X69760, S.tubersum rbcS2 gene for ribulose-(1,5)-biphosphate carboxylase/oxygenase small subunit, 1629 bp DNA.

Schreier PH (1992) GenBank Accession No. X69759, S.tubersum rbcS1 gene for ribulose-(1,5)-biphosphate carboxylase/oxygenase small subunit, 3323 bp DNA.

Wolter FP, Fritz CC, Willmitzer L, Schell J and Schreier PH (1988) GenBank Accession No. J03613, Potato (S.tuberosum) ribulose biphosphate carboxylase (rbcS) mRNA, complete cds, 546 bp mRNA.

Koncz C and Schell J (1986) The promoter of $T_L$-DNA gene 5 controls the tissue-specific expression of chimaeric genes carried by a novel type of *Agrobacterium* binary vector. Mol Gen Genet 204: 383-396.

Schell J, Kaulen H, Kreuzaler F, Eckes P, Rosahl S, Willmitzer L, Spena A, Baker B, Herrera-Estrella L and Fedoroff N (1985) Transfer and regulation of expression of chimeric genes in plants. Cold Spring Harb Symp Quant Biol 50: 421-431.

Goodwin TW and Mercer EI. (1983). Introduction to plant biochemistry. (Oxford: Pergamon Press).

Kimball BA (1983) Carbon dioxide and agricultural yield: an assemblage and analysis of 430 prior observations Agronomy Journal. 779-788.

Somerville et al. (1980) Photorespiration mutants of *Arabidopsis thaliana* deficient in serine-glyoxylate aminotransferase activity. Proc Natl Acad Sci U S A. 77(5): 2684-2687.

Lord JM (1972) Glycolate oxidoreductase in *Escherichia coli*. Biochimica et Biophysica Acta 267: 227-237.

Nelson EB and Tolbert NE (1970) Glycolate dehydrogenase in green algae. Archives of Biochemistry & Biophysics 141: 102-110.

Kohn LE (1968) Tartaric acid metabolism VIII. Crystalline tartronic semialdehyde reductase. Journal of Biological Chemistry 243: 4426-4433.

Glycolate dehydrogenase (GDH), International union of biochemistry and molecular biology (IUBMB) number EC 1.1.99.14.

Glycolate oxidase (GO), International union of biochemistry and molecular biology (IUBMB) number EC 1.1.3.15.

Glyoxylate oxidoreductase (GOR), International union of biochemistry and molecular biology (IUBMB) No. EC 1.1.1.26.

Glyoxylate oxidoreductase (GOR), International union of biochemistry and molecular biology (IUBMB) No. EC 1.1.1.79.

Kebeish, Rashad, 2006, "Construction and molecular analysis of genetically modified $C_3$ plants expressing a glycolate oxidizing pathway inside the chloroplast," Dissertation presented toward qualification for a Doctorate in Natural Sciences granted by the Rheinisch-Westfälischen Technischen Hochschule Aachen (RWTH Aachen University), Faculty representatives Univ.-Prof. Dr. F.M. Kreuzaler and Dr. C. Peterhänsel, oral defense on Apr. 10, 2006.

Bari, Md. Rafijul, 2004, "A novel approach for the suppression of photorespiration in $C_3$ plants by gene transfer," Dissertation presented toward qualification for a Doctorate in Natural Sciences granted by the Rheinisch-Westfälischen Technischen Hochschule Aachen (RWTH Aachen University), Faculty representatives Univ. Prof. Dr. F. Kreuzaler and Univ. Prof. Dr. U. Priefer, oral defense on Apr. 20, 2004.

\* cited by examiner

FIGURES

The main plant photorespiratory cycle. RUBISCO = Ribulose-1,5-bis-phosphate Carboxylase/Oxygenase; PGP = Phosphoglycolate Phosphatase; GO = Glycolate Oxidase; GGAT = Glutamate Glyoxylate Aminotransferase; SS = Serin-Synthase; SGAT = Serine Glyoxylate Aminotransferase; HPR = Hydroxypyruvate-Reductase; GK = Glycerate Kinase The $C_4$ pathway (as established in maize). CA = Carbonic Anhydrase; PEP = phosphoenolpyruvate; PEPC = Phosphoenolpyruvate Carboxylase; OAA = oxaloacetate; MDH = Malate Dehydrogenase; ME = Malic Enzyme; RuBP = ribulose-1,5-bisphosphate; Pyr = pyruvate; PPDK = pyruvate-$P_i$-dikinase The C$_4$-like unicellular pathway. OAA = oxaloacetate PEP = phosphoenolpyruvate; PYR = pyruvate. PEPC = Phosphoenolpyruvate Carboxylase; PCK = Phosphoenolpyruvate Carboxykinase; ME = Malic Enzyme; PPDK = pyruvate-P$_i$-dikinase; PPT = Triose Phosphate Translocator The bacterial glycolate-utilizing pathway. GO = Glycolate Oxidase; GCL = Glyoxylate Carboligase; TSR = Tartronic Semialdehyde Reductase Enzymatic activities written in bold are introduced in the plant chloroplast by transformation.

PGP = Phosphoglycolate Phosphatase; GO = Glycolate Oxidase; GCL = Glyoxylate Carboligase; TSR = Tartronic Semialdehyde Reductase; GK = Glycerate Kinase; RuBP = ribulose-1,5-bisphosphate.

Figure 6

LB, RB = left and right border, Pnos = Nopalin Synthase Promoter, *npt*II = Neomycin Phosphotransferase, pAnos = Nopalin Synthase Polyadenylation Signal, SAR = Scaffold Attachment Region, P35SS/pA35S = Transcriptionally enhanced Promoter and Polyadenylation Signal of the 35S gene from cauliflower mosaic virus, TL = tobacco etch virus 5'untranslated region, cTP = Potato Ribulose-1,5-bisphosphate Carboxylase Chloroplast Transit Peptide.

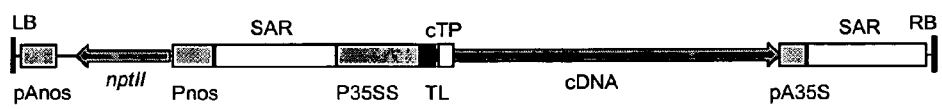

Figure 7

LB, RB = left and right border, Pnos = Nopalin Synthase Promoter, *npt*II = Neomycin Phosphotransferase, pAnos = Nopalin Synthase Polyadenylation Signal, SAR = Scaffold Attachment Region, P35SS/pA35S = Transcriptionally enhanced Promoter and Polyadenylation Signal of the 35S gene from cauliflower mosaic virus, TL = tobacco etch virus 5'untranslated region, cTP = Potato Ribulose-1,5-bisphosphate Carboxylase Chloroplast Transit Peptide, GCL = *Escherichia coli* Glyoxylate Carboligase, TSR = *Escherichia coli* Tartronic Semialdehyde Reductase, ColE1 ori = Origin of Replication for propagation in *Escherichia coli*, RK2 ori = Origin of Replication for propagation in *Agrobacterium tumefaciens*, bla = β-Lactamase.

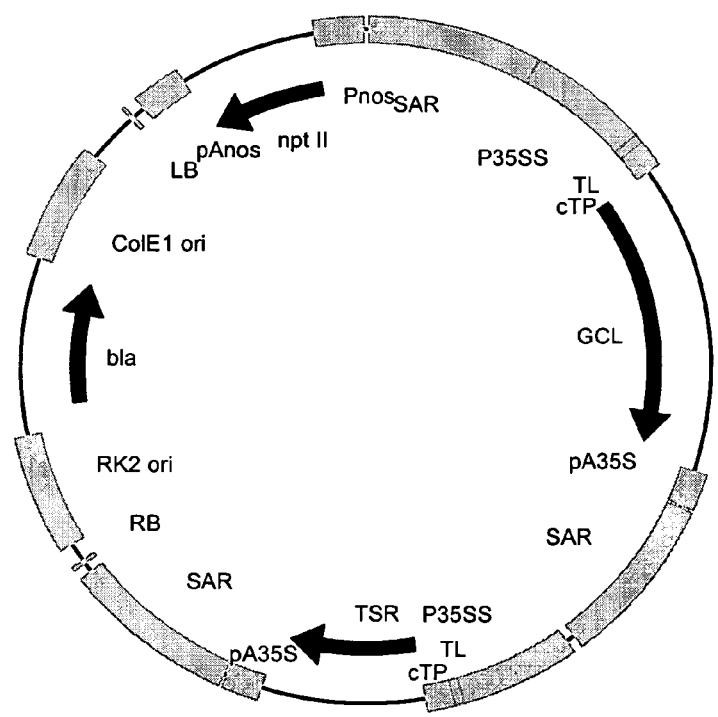

A construct for the polycistronic plastidic expression of the components of the pathway. GO = Glycolate oxidase; glcD = glcD subunit of *E. coli* GO; glcE = glcE subunit of *E. coli* GO; glcF = glcF subunit of *E. coli* GO; TSR = Tartronic Semialdehyde Reductase; GCL = Glyoxylate Carboligase.

Figure 9

Glycolate dehydrogenase activity of an *Arabidopsis thaliana* homologue to the *E. coli* glc operon. Shown is the production of glyoxylate in a glycolate dehydrogenase assay as disclosed before (Lord, 1972). Proteins were overexpressed as His-tagged versions in *E. coli*. AtglcD = *Arabidopsis thaliana* homologue to the *E. coli* glc operon. unrel. = unrelated protein that was expressed in parallel; - co-factor = assay in the absence of organic co-factors

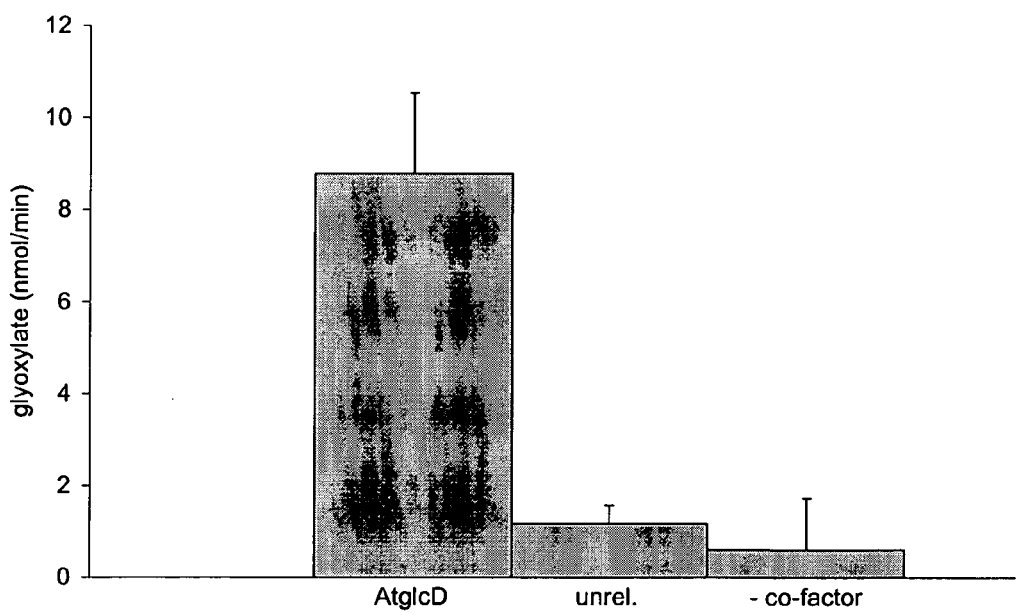

METHOD FOR PRODUCING PLANTS WITH SUPPRESSED PHOTORESPIRATION AND IMPROVED $CO_2$ FIXATION

RELATED APPLICATIONS

The present application claims priority to International Application No. PCT/EP03/05398, filed on May 23, 2003, which claims priority to European Application No. 02011578.8 filed on May 27, 2002, each of which is incorporated by reference herein in its entirety.

FIELD OF THE INVENTION

The present invention is directed to plants exhibiting suppressed photorespiration and improved $CO_2$ fixation and methods for producing such plants.

BACKGROUND OF THE INVENTION

Many efforts have recently been made to improve growth and resistance of crop plants. Some of the most important crop plants, e.g. rice, wheat, barley, potato, belong to the so-called $C_3$ plants. Only a few important crop plants, like corn and sugar cane, are $C_4$ plants. $CO_2$ fixation in $C_3$ plants is primarily catalyzed by the enzyme ribulose-1,5-bisphosphate carboxylase (RUBISCO) which is located in the chloroplasts. The enzyme RUBISCO catalyzes two reactions: carboxylation and oxygenation of ribulose-1,5-bisphosphate. The product of the first reaction are two molecules of 3-phosphoglycerate which enter the Calvin cycle to form starch and ribulose-1,5-bisphosphate. The products of the oxygenase reaction are one molecule each of 3-phosphoglycerate and phosphoglycolate (Goodwin and Mercer, 1983). The latter is converted to 3-phosphoglycerate in a biosynthetic pathway known as photorespiration (see FIG. 1). In the course of this complex sequence of reactions, one molecule of $CO_2$ is released and lost for the plant. This loss of $CO_2$ reduces the formation of sugars and polysaccharides in the plant and thus reduces their productivity. Furthermore, $NH_3$ is released which has to be refixed. These effects are exacerbated further when plants are grown under suboptimal water supply. Here, leaf stomata are closed and the intercellular oxygen concentration rises because of molecular oxygen released from the light reactions of photosynthesis. High amounts of phosphoglycolate are produced that enter the photorespiratory cycle. It has been estimated that plants lose approximately 25% of the already fixed carbon due to photorespiration. This cycle is absolutely intrinsic to all $C_3$ plants because of the oxygenase activity of RUBISCO (Leegood et al., 1995; Tolbert, 1997).

The importance of photorespiration for plant growth and yield has been shown by several experiments where the atmospheric $CO_2$ concentration has been artificially raised in greenhouse experiments. Significant increases in the performance of several crop species have been observed already when the $CO_2$ concentration is doubled (Kimball, 1983; Arp et al., 1998). However, this approach is not applicable to the large, open areas used for agricultural production.

$C_4$ plants have evolved a mechanism to avoid these losses. They have employed enzymes already present in their $C_3$ ancestors, but changed the degree of expression as well as the localisation on a subcellular and cell-type specific level. By separating primary and secondary carbon fixation in two different tissues, they drastically increase the local $CO_2$ concentration at the site of RUBISCO activity. Shortly, the first $CO_2$ fixation takes place in the cytoplasm of mesophyll cells and is catalyzed by PEPC, an enzyme without intrinsic oxygenase activity and significantly higher affinity to its substrate compared to RUBISCO. The resulting $C_4$ acid diffuses into the gas tight bundle sheath and is here decarboxylated to liberate $CO_2$. The remaining monocarbonic acid serves to regenerate the primary $CO_2$ acceptor in the mesophyll. This $CO_2$ concentration mechanism results in a complete suppression of photorespiration and an oxygen-insensitive photosynthesis (Kanai and Edwards, 1999). A similar mechanism with a temporal, instead of spatial, separation of enzymatic activities is applied by the crassulacean acid metabolism (CAM) plants (Cushman and Bohnert, 1999).

Beside these mechanisms depending on the cooperation of two different cell types some aquatic plants have developed $C_4$-like mechanisms working within one cell. Here, primary and secondary $CO_2$ fixation take place in one cell, but in different compartments. Whereas PEPC activity is restricted to the cytoplasm, $CO_2$ release and refixation similar to $C_4$ plants take place in the chloroplast. This unicellular $C_4$-like pathway results in a partial suppression of photorespiration with reduced sensitivity to oxygen (Reiskind et al., 1997).

Several attempts have been described to transfer $C_4$- or $C_4$-like pathways or components of this pathway to $C_3$ plants. Mostly, overexpression of PEPC has been used so far. Three groups applied expression of the maize PEPC cDNA or gene under control of different promoters (Hudspeth et al., 1992; Kogami et al., 1994; Ku et al., 1999). Although increases in PEPC activity levels up to 100-fold were detected with the complete intact maize gene in rice (Ku et al., 1999), there were only weak impacts on plant physiology and growth performance (Matsuoka et al., 2001, see also EP-A 0 874 056). Recently, the overexpression of PEPC and malate dehydrogenase from Sorghum in potato has been described, but in this case expression levels were low and no modification of photosynthetic parameters could be observed (Beaujean et al., 2001). PEPC cDNAs from bacterial source have been overexpressed in potato by Gehlen et al. (1996) with some minor impact on photosynthetic parameters. The combination of this enzyme with the additional overexpression of a $NADP^+$-malic enzyme (ME) from *Flaveria pringlei* targeted to the chloroplast enhanced these effects without any impact on plant growth or yield (Lipka et al., 1999). For rice, it has been recently described that the overexpression of a phosphoenolpyruvate carboxykinase (PCK) from *Urochloa panicoides* targeted to the chloroplast results in the induction of endogenous PEPC and the establishment of a $C_4$-like cycle within a single cell. However, no enhanced growth parameters were observed (Suzuki et al., 2000; see also WO 98/35030).

Therefore, despite several attempts to improve $CO_2$ fixation and reduce photorespiration, until now no method has been provided that leads to an improvement of growth, productivity, and/or yield for agricultural crop plants. All these attempts were aiming to concentrate $CO_2$ at the site of fixation in order to suppress the oxygenase activity of RUBISCO.

Many bacteria have evolved biochemical pathways to metabolize glycolate, the primary product of the oxygenase activity of RUBISCO. For *Escherichia coli*, this pathway has been described in great detail (Lord, 1972; Pellicer et al., 1996). *E. coli* is capable of growing on glycolate as the sole carbon source. As summarised in FIG. 4, glycolate is first oxidized to glyoxylate. This reaction is brought about by a multiprotein complex that is capable of oxidizing glycolate in an oxygen-independent manner. The proteins necessary for glycolate oxidation in *E. coli* have been analysed and it has been shown that the open reading frames D, E, and F of the glycolate oxidase operon glc are encoding the components of the active enzyme. In the next reaction step, two molecules of glyoxylate are ligated by glyoxylate carboligase (GCL) to form tartronic semialdehyde (TS) and $CO_2$ is released in this reaction. TS is further converted to glycerate by TS reductase (TSR). Glycerate is integrated into the bacterial basal carbon metabolism.

A similar pathway is also applied as a photorespiratory cycle in some green algae and cyanobacteria (Nelson and Tolbert, 1970; Ramazanov and Cardenas, 1992). In this case, glycolate oxidation is seemingly catalysed by glycolate dehydrogenase located inside the mitochondria. Again, this enzyme is not oxygen-dependent and uses organic electron acceptors like Nicotin-Adenosin-Dinucleotid ($NAD^+$) instead. The further metabolism of glyoxylate seems to be similar to the pathway as described for *E. coli*.

SUMMARY OF THE INVENTION

The present invention relates to methods for suppressing photorespiration and increasing productivity and/or yield in crop plants. Accordingly, the present invention provides methods for producing plants with suppressed photorespiration and improved $CO_2$ fixation. In particular, the invention relates to a re-use of phosphoglycolate produced in photorespiration. The reaction product is converted to a component that may be reintegrated into the plant assimilatory metabolism inside the chloroplast. This is accomplished by the transfer of genes derived from glycolate-utilizing pathways from bacteria, algae, plants and/or animals including humans into the plant nuclear and/or plastidial genome. The methods of the invention lead to reduced photorespiration in $C_3$ plants and, therefore, are of great benefit for food production, especially but not exclusively under non-favourable growth conditions.

In one nonlimiting embodiment, the present invention provides a method for the production of plants with suppressed photorespiration and improved $CO_2$ fixation, such that the method includes introducing one or more nucleic acids into a plant cell, plant tissue or plant, wherein the introduction of the nucleic acid(s) results in a de novo expression of polypeptides having the enzymatic activities of (i) glycolate oxidase or glycolate dehydrogenase, (ii) glyoxylate carboligase and (iii) tartronic semialdehyde reductase.

BRIEF EXPLANATION OF THE FIGURES

FIG. 6: Schematic representation of exemplary T-DNA constructs useful for plant transformation FIG. 7: Schematic representation of exemplary vector constructs useful for plant transformation FIG. 9: Glycolate dehydrogenase activity of an *Arabidopsis thaliana* homologue to the *E. coli* glc operon.

DETAILED DESCRIPTION OF THE INVENTION

The present invention provides methods for the production of plants with suppressed photorespiration and improved $CO_2$ fixation, the methods comprising introducing into a plant cell, plant tissue or plant one or more nucleic acids, wherein the introduction of the nucleic acid(s) results in a de novo expression of polypeptides having the enzymatic activities of (i) glycolate oxidase or glycolate dehydrogenase, (ii) glyoxylate carboligase and (iii) tartronic semialdehyde reductase.

In particular, the invention relates to a re-use of the phosphoglycolate produced in photorespiration. The reaction product will be converted to a component that may be reintegrated into the plant assimilatory metabolism inside the chloroplast. This will be accomplished by the transfer of genes derived from glycolate-utilizing pathways from bacteria, algae, plants and/or animals including humans into the plant nuclear and/or plastidial genome. The present invention provides a reduction of photorespiration in $C_3$ plants and by this is of great benefit for food production, especially but not exclusively under non-favourable growth conditions.

The present invention provides methods to install or introduce a glycolate oxidizing activity inside the chloroplast. For this, several enzymes have to be transferred to the chloroplast. This can be brought about, for example, by nuclear transformation of plant cells, plant tissue or plants with the coding sequence of the respective protein fused to a chloroplast transit peptide or by direct transformation of the chloroplast genome. Promoters controlling the expression of the respective transgenes may be, for example, constitutive or controlled by environmental or technical means. The enzymes may be transferred to plant cells, plant tissue or plants, for example, on single plasmid constructs or independently on several constructs. General techniques for gene integration are well known in the art and include *Agrobacterium*-mediated transfer, electroporation, microinjection, or chemical treatment. The present invention is applicable to any plant, plant cells (including, for example, algal cells), or plant tissues. In one non-limiting embodiment, the plant is a $C_3$ plant. In other non-limiting embodiments, the plant is a potato or tobacco plant.

Figure 1:
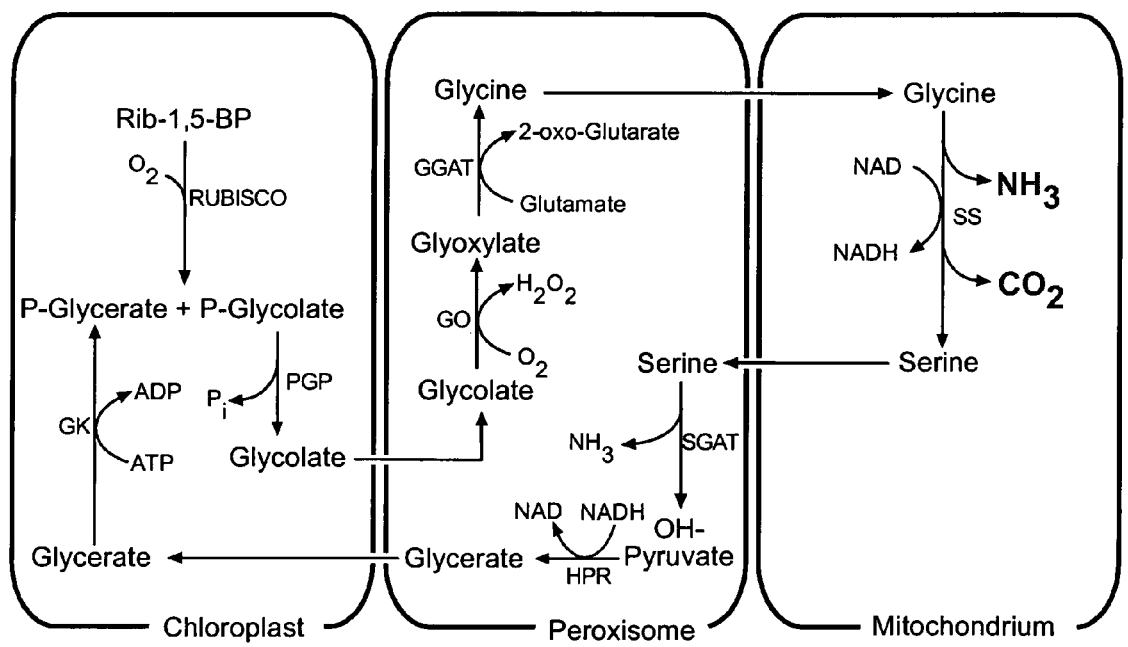
FIG. 1: The photorespiratory pathway
Figure 2:
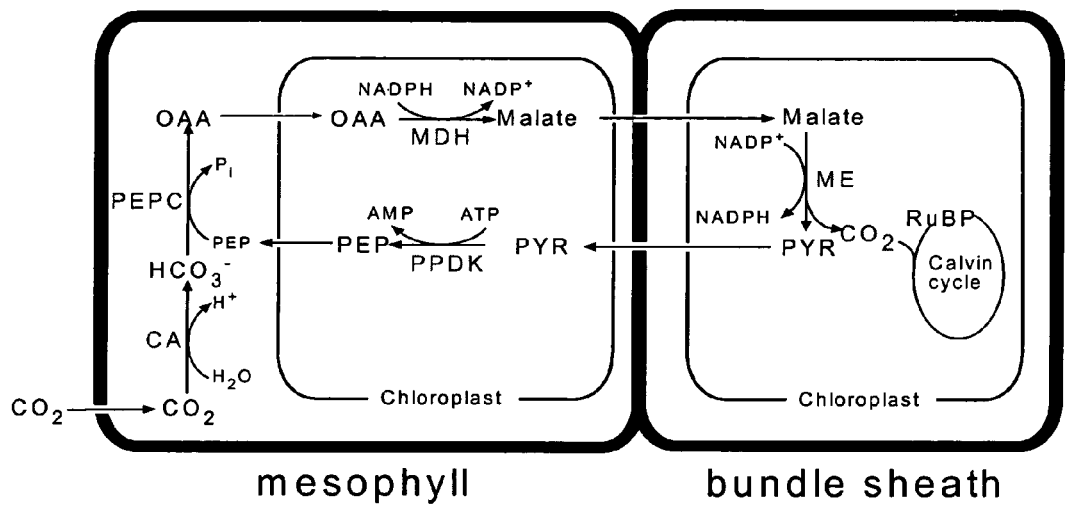
FIG. 2: The $C_4$-pathway
Figure 3:
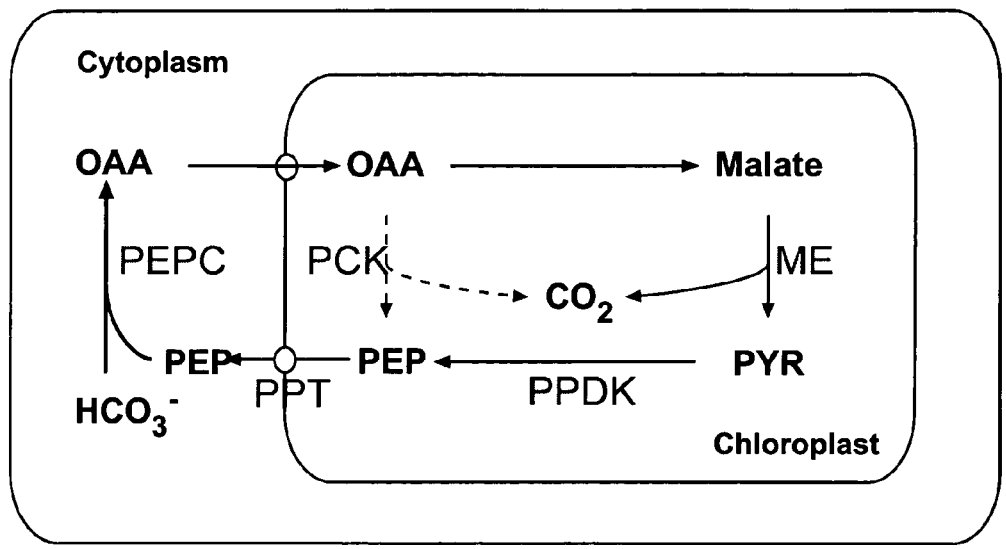
FIG. 3: The $C_4$-like unicellular pathway
Figure 4:
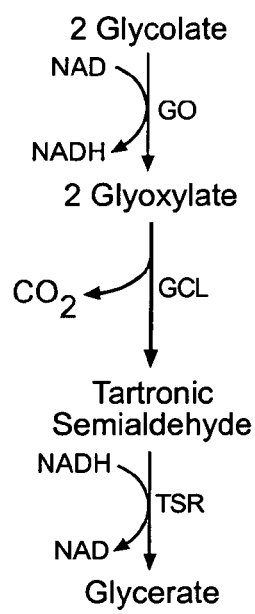
FIG. 4: The bacterial glycolate-utilizing pathway
Figure 5:
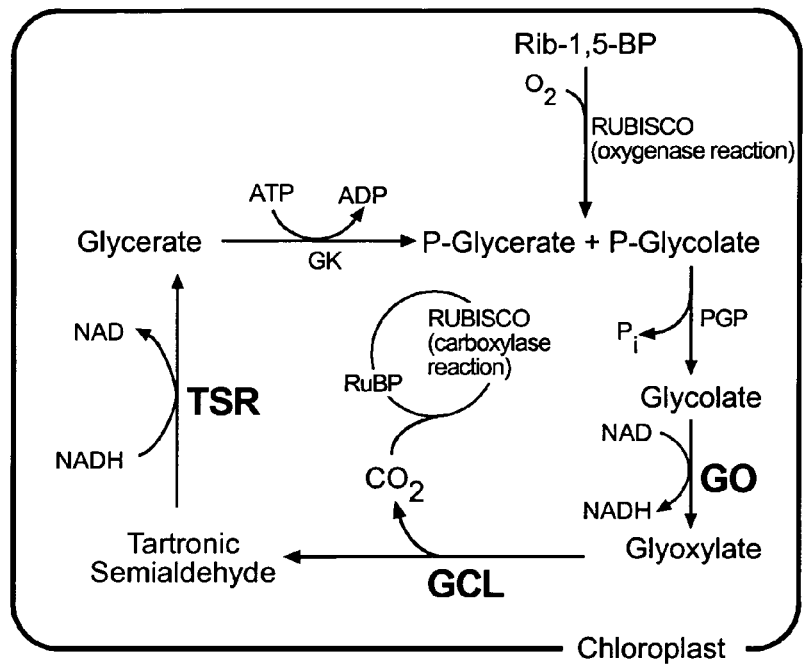
FIG. 5: A novel plastidial pathway in accordance with the present invention

A pathway in accordance with the present invention is shown in exemplary FIG. 5: The first protein in the new biochemical pathway is an enzyme catalysing the oxidation of glycolate in an oxygen-independent manner with organic cofactors. Oxidases useful for this purpose include, for example, bacterial glycolate oxidases and algal glycolate dehydrogenases as well as mammal glyoxylate reducing activities and functional homologues derived from plants.

TABLE 1

| Glycolate-oxidising enzymes | |
|---|---|
| Enzyme | Activity |
| Glycolate oxidase (GO; EC 1.1.3.15) | oxygen dependent peroxisomal plant photorespiration |
| Glyoxylate oxidoreductase (GOR; EC 1.1.1.26/79) | NAD/NADP dependent cloned from human source equilibrium unclear |
| Glycolate dehydrogenase (GDH; EC 1.1.99.14) | NAD dependent = *E. coli* glycolate oxidase activity described for algal mitochondria |

The protein may be constituted, for example, by one or multiple polypeptides. Importantly, the use of enzymes from these sources will prevent the formation of reactive oxygen species that are produced by the higher plant glycolate oxidases localized inside the peroxisomes.

In preferred non-limiting embodiments, polypeptides having the enzymatic activity of a glycolate oxidase are those encoded by the *E. coli* glc operon. Preferred non-limiting embodiments use polypeptides which comprise the amino acid sequences of SEQ ID NOS: 2 (Glc D), 4 (Glc E) and 6 (Glc F). Therefore, nucleic acids comprising a polynucleotide sequence of SEQ ID NOS: 1, 3 and 5 can be used in accordance with the present invention.

In another non-limiting embodiment, human glyoxylate reductase having the activity of a glycolate dehydrogenase can be used. In a preferred non-limiting embodiment, the human glyoxylate reductase comprises the amino acid sequence of SEQ ID NO: 8. Therefore, a nucleic acid comprising the polynucleotide sequence of SEQ ID NO: 7 can also be used in accordance with the present invention.

In other non-limiting embodiments, the homologues derived from *Arabidopsis thaliana* or other higher plant sources can be used in place of the above-mentioned *E. coli* polypeptides encoded by the glc operon. A preferred *Arabidopsis thaliana* homologue comprises the amino acid sequence of SEQ ID NO: 10 and is encoded by a nucleic acid comprising the polynucleotide sequence of SEQ ID NO: 9.

In one embodiment, the second protein is an enzyme catalyzing the formation of tartronic semialdehyde. The tartronic semialdehyde may be formed from two molecules of glyoxylate under release of inorganic $CO_2$. Glyoxylate carboligase from bacterial or algal source, for example, as well as functional homologues from other sources are suitable for this purpose.

A preferred polypeptide having the activity of a glyoxylate carboligase comprises the amino acid sequence of SEQ ID NO: 12. Therefore, a nucleic acid comprising the polynucleotide sequence of SEQ ID NO: 11 can be used in accordance with the present invention.

In one embodiment, the third protein is an enzyme catalyzing the formation of glycerate from tartronic semialdehyde. Suitable enzymes for this purpose include, for example, tartronic semialdehyde reductase from bacterial or algal source, for example, as well as functional homologues from other sources.

A preferred polypeptide having the activity of a tartronic semialdehyde reductase comprises the amino acid sequence of SEQ ID NO: 14. Therefore, a nucleic acid comprising the polynucleotide sequence of SEQ ID NO: 13 can be used in accordance with the present invention.

For the purpose of expressing the nucleic acids which encode the polypeptides having the enzymatic activities in accordance with the present invention in plant cells, any convenient regulatory sequence can be used. In a non-limiting embodiment, the regulatory sequence provides transcriptional and translational initiation as well as termination regions. The transcriptional initiation may be constitutive or inducible. In a non-limiting embodiment, the coding region is operably linked to such regulatory sequences. Suitable regulatory sequences are represented, for example, by the constitutive 35S promoter which may be used for dicotyledonous plants. For monocotyledonous plants the constitutive ubiquitin promoter, for example, can be used. In a specific non-limiting embodiment, the maize ubiquitin promoter (GenBank: gi19700915) is employed as the regulatory sequence. Examples for inducible promoters include, without limitation, the light inducible promoters of the small subunit of RUBISCO, such as for example, the tomato rbcS promoter (GenBank: gi22624), and the promoters of the "light harvesting complex binding protein (lhcb)", such as for example, the tobacco lhcb promoter (GenBank: gi1890636).

A polypeptide having the enzymatic activities in accordance with the present invention may comprise an amino acid sequence that targets the polypeptide. In particular, non-limiting embodiments, the amino acid sequence targets the polypeptide to the chloroplast, the chloroplast membrane and/or the cytoplasm. Suitable targeting sequences are known to the person skilled in the art. In a preferred embodiment, the chloroplast transit peptide derived from the ribulose-1,5-bisphosphate carboxylase gene from *Solanum tuberosum* (GenBank: G68077, amino acids 1-58) is used for targeting the polypeptides according to the present invention to the chloroplasts.

In another non-limiting embodiment, the polypeptide is directly targeted to the chloroplast using transformation of the chloroplast genome. In a specific non-limiting embodiment, the chloroplast is transformed by particle bombardment of leaf sections and integration by homologous recombination. Suitable vectors and selection systems are known to the person skilled in the art. The coding sequences for the polypeptides may be transferred, for example, in individual vectors or in one construct. The individual open reading frames may be fused to one or several polycistronic RNAs with ribosome binding sites added in front of each individual open reading frame in order to allow independent translation.

Phosphoglycolate phosphatase and glycerate kinase as well as RUBISCO are abundant enzymes inside plant chloroplasts. Thus, in other embodiments, these enzymes do not have to be transferred to chloroplasts to enable function of the novel biochemical pathway.

Introduction of the pathway in accordance with the present invention allows the direct reintegration of $CO_2$ released during the reaction pathway into the photosynthetic reactions. Accordingly, inorganic carbon is not lost in the mitochondria as described for photorespiratory reactions. Therefore, in accordance with the present invention, the products of photorespiration suppress photorespiration by increasing the $CO_2$ concentration at the site of fixation.

Exemplary methods to confirm that the novel pathway is functional inside the plant chloroplast include: (1) Studying whether the genes are expressed and the proteins accumulate inside the chloroplast; (2) Studying whether the metabolic intermediates of the pathway accumulate in the plant cell; (3) Studying any changes in the photosynthetic properties of the transformant by measurement of the photosynthetic property, which preferably includes the determination of the $CO_2$ compensation point by gas exchange measurements; and (4) Studying growth, biomass production and yield of the plants under different growth conditions, preferably under non-favourable conditions for $C_3$-plants.

The present invention provides plant cells, plant tissues, and plants. The plant, plant tissue, or plant cell comprises one or more nucleic acids which encode polypeptides having the enzymatic activities of (i) glycolate oxidase or glycolate dehydrogenase, (ii) glyoxylate carboligase and (iii) tartronic semialdehyde reductase.

Preferred embodiments of the nucleic acids introduced into the plant cells, plant tissues or plants are mentioned above.

Because of the enhanced photosynthetic potential, the plants that are produced in accordance with the present invention achieve one or more of the following properties:

elevated yield per dry weight, improved drought and heat resistance, enhanced nitrogen-use efficiency, and reduced requirements for fertilization. These measurements are determined in comparison to control plants (for example, plants in which a nucleic acid of the invention has not been introduced).

The present invention will be better understood by the following exemplary teachings. The examples set forth herein do not and are not intended to limit in any manner the present invention.

EXAMPLES

Example 1

Amplification of Genes from *E. coli* involved in Glycolate Metabolism

The genes encoding tartronic semialdehyde reductase, glyoxylate carboligase, and the open reading frames encoding the D, E, and F polypeptides from the glycolate oxidase operon were amplified from the genome of *E. coli* using the PCR method. Sequences were derived from public databases. The oligonucleotides were complementary to the start and the end of the coding regions, respectively, as provided in the sequence listing herein.

Example 2

Amplification of a cDNA Encoding Human Glyoxylate Reductase

The cDNA encoding glyoxylate reductase was amplified from human liver mRNA using the "Reverse-Transcriptase-PCR-method". Sequences were derived from scientific literature (Rumsby and Cregeen, 1999). The mRNA was reverse transcribed using oligo-dT oligonucleotides as a start and the PCR was performed with oligonucleotides complementary to the start and the end of the coding regions, respectively, as provided in the sequence listing herein.

Example 3

Amplification of a cDNA Encoding a Homologue to the *E. coli* glcD open Reading Frame from *Arabidopsis thaliana*

An open reading frame with homology on the protein level to the glcD open reading frame from the glc operon from *E. coli* was identified as a genomic sequence from *Arabidopsis thaliana* in a public database. RNA was isolated from young leaf tissue and the coding sequence was amplified using the "Reverse-Transcriptase-PCR-method". The mRNA was reverse transcribed using oligo-dT oligonucleotides as a start and the PCR was performed with oligonucleotides complementary to the start and the end of the coding regions, respectively, as provided in the sequence listing herein.

Example 4

Activity Measurement of the His-Tagged Versions Overexpressed in *E. coli*

The coding sequences of the genes as described in Examples 1–3 were cloned into the vector pET22b(+) [Novagen, Darmstadt, Germany] as a N-terminal translational fusion to six histidine residues. Proteins were overexpressed in *E. coli* strain ER2566 [NEB, Beverly, Mass., USA] and in part purified on a $Ni^{2+}$-chelate-affinity matrix [Qiagen, Hilden, Germany] following the manufacturer's instructions.

Activities of tartronic semialdehyde reductase and glyoxylate carboligase were measured in crude extracts derived from overexpressing and non-overexpressing strains by techniques as disclosed before (Kohn, 1968; Chang et al., 1993). The results indicate that the proteins sustain their enzymatic function in translational fusion to six histidine residues and that the amplified sequences encode the respective enzymatic activities.

The activity of the *Arabidopsis* homologue to the *E. coli* glc operon (SEQ ID NO: 10) was measured in crude extracts from overexpressing and non-overexpressing bacterial strains as disclosed before (Lord, 1972). The results indicate that the *Arabidopsis* homologue is a true glycolate dehydrogenase capable of oxidising glycolate in the presence of organic cofactors. A diagram showing the relative activities is shown in FIG. 9.

Example 5

Construction of Expression Vectors for Plants

For plant transformation, the gene constructs were inserted into the binary plant expression vector pTRAKc, a derivative of pPAM (GenBank: AY027531). The expression cassette was flanked by the scaffold attachment region of the tobacco RB7 gene (GenBank: U67919). The nptII cassette of pPCV002 (Koncz and Schell, 1986) was used for selection of transgenic plants. Expression of genes is under constitutive control of the transcriptionally enhanced CaMV 35S promoter (Reichel et al., 1996). Proteins were expressed as a translational fusion to a chloroplast transit peptide derived from the ribulose-1,5-bisphosphate carboxylase gene from *Solanum tuberosum* (Gen Bank: G68077, amino acids 1–58). A schematic representation of the T-DNA is given in FIG. 6. Single constructs for tartronic semialdehyde reductase (TSR) and glyoxylate carboligase (GCL) were cloned into the MluI and Ecl136II restriction sites of the vector. A construct containing both genes was made by cutting a 4629 bp fragment from the construct containing the TSR coding sequence with restriction enzymes AscI and ScaI and ligating it into the vector containing the GCL coding sequence cut with restriction enzymes PmeI and ScaI. Before ligation, the protruding ends of the AscI restriction site were blunted with Klenow polymerase. A schematic representation of the final vector construct is given in FIG. 7. The vector is named pTRAc-rbCS1-cTP-TSR/GCL.

Example 6

Introduction of the Expression Vectors into Plants

The vector pTRAc-rbCS1-cTP-TSR/GCL was introduced into *Agrobacterium tumefaciens* strain GV3101 supplied by Dr. Koncz, Max-Planck-Institute for Breeding Research, Cologne, Germany via electroporation. Leaf sections of tobacco were transformed following techniques as described in (Schell et al., 1985). Calli were selected for resistance to Kanamycin and plants were regenerated from resistant calli. Potential transgenic lines were selected for the presence of the transgenes integrated into the genome using the PCR method. Accumulation of the transcripts and proteins, respectively, was shown using RT-PCR or Western analyses with antibodies to the C-terminal six-histidine fusion and highly expressing lines were selected.

Example 7

Plastidic Transformation of Tobacco

Figure 8:
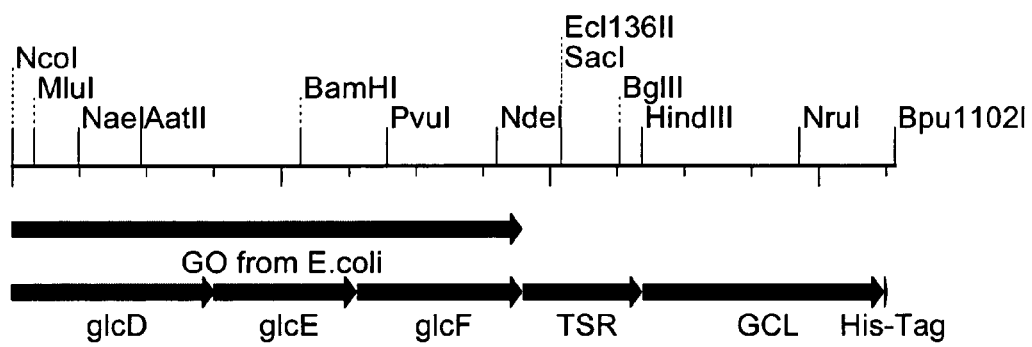
FIG. 8: A construct for the polycistronic plastidic expression of the components of the pathway

A vector was constructed allowing the simultaneous expression of all polypeptides necessary for the establishment of the proposed pathway by transformation of the chloroplast genome of tobacco. The part of the glc operon from *E. coli* encoding the glcD, glcE, and glcF polypeptides was amplified using the PCR method. The coding sequences for tartronic semialdehyde reductase (TSR) and glyoxylate carboligase (GCL) from *E. coli* were amplified and shine dalgarno sequences were added upstream of the coding sequence using the PCR method. A C-terminal translational fusion to six histidines was added to the GCL coding sequence. In each case oligonucleotides homologous to the beginning and the end of the respective coding sequences with extensions for the addition of the mentioned sequence elements were used. The complete construct was cut with NcoI and Bpu1102lI and transferred into a vector for plastidic transformation that was cut with NcoI and XbaI (Bock, 2001). Before ligation, the protruding ends of the XbaI and Bpu1102I restriction sites were blunted with Klenow polymerase. A schematic representation of the vector insert is given in FIG. 8.

Chloroplasts of *Nicotiana tabacum* cv. Petit Havanna plants were transformed using particle bombardment. Transformed lines were selected using spectinomycin and streptomycin antibiotics as described before (Bock, 2001).

The present invention is not to be limited in scope by the specific embodiments described above. Many modifications of the present invention, in addition to those specifically recited above would be apparent to the skilled artisan using the teachings of the instant disclosure. Such modifications are intended to fall within the scope of the appended claims. All publications, patents and patent publications, cited in the instant specification are herein incorporated by reference in their entireties.

LITERATURE

Arp W J, Van Mierlo J E M, Berendse F and Snijders W (1998) Interactions between elevated CO2 concentration, nitrogen and water: Effects on growth and water use of six perennial plant species. Plant, Cell & Environment 21: 1–11.

Beaujean A, Issakidis-Bourguet E, Catterou M, Dubois F, Sangwan R and Sangwan-Norreel B (2001) Integration and expression of Sorghum C-4 phosphoenolpyruvate carboxylase and chloroplastic NADP(+)-malate dehydrogenase separately or together in C-3 potato plants. Plant Science 160: 1199–1210.

Bock R (2001) Transgenic plastids in basic research and plant biotechnology. J Mol Biol 312: 425–438.

Chang Y Y, Wang A Y and Cronan J E, Jr. (1993) Molecular cloning, DNA sequencing, and biochemical analyses of *Escherichia coli* glyoxylate carboligase. An enzyme of the acetohydroxy acid synthase-pyruvate oxidase family. Journal of Biological Chemistry 268: 3911–3919.

Cushman J C and Bohnert H J (1999) Crassulacean acid metabolism: molecular genetics. Annu Rev Plant Physiol Plant Mol Biol 50: 305–332.

Gehlen J, Panstruga R, Smets H, Merkelbach S, Kleines M, Porsch P, Fladung M, Becker I, Rademacher T, Hausler R E and Hirsch H J (1996) Effects of altered phosphoenolpyruvate carboxylase activities on transgenic C3 plant *Solanum tuberosum*. Plant Molecular Biology 32: 831–848.

Goodwin T W and Mercer E I. (1983). Introduction to plant biochemistry. (Oxford: Pergamon Press).

Hudspeth R L, Grula J W, Dai Z, Edwards G E and Ku M S B (1992) Expression of maize phosphoenolpyruvate carboxylase in transgenic tobacco. Plant Physiol 98: 458–464.

Kanai R and Edwards G E (1999). The Biochemistry of $C_4$ Photosynthesis. In $C_4$ Plant Biology, R. K. Monson, ed (San Diego: Academic Press), pp. 49–87.

Kimball B A (1983) Carbon dioxide and agricultural yield: an assemblage and analysis of 430 prior observations Agronomy Journal. 779–788.

Kogami H, Shono M, Koike T, Yanagisawa S, Izui K, Sentoku N, Tanifuji S, Uchimiya H and Toki S (1994) Molecular and physiological evaluation of transgenic tobacco plants expressing a maize phosphoenolpyruvate carboxylase gene under the control of the cauliflower mosaic virus 35S promoter. Transgenic Research 3: 287–296.

Kohn L E (1968) Tartaric acid metabolism VIII. Crystalline tartronic semialdehyde reductase. Journal of Biological Chemistry 243: 4426–4433.

Koncz C and Schell J (1986) The promoter of $T_L$-DNA gene 5 controls the tissue-specific expression of chimaeric genes carried by a novel type of *Agrobacterium* binary vector. Mol Gen Genet 204: 383–396.

Ku M S, Agarie S, Nomura M, Fukayama H, Tsuchida H, Ono K, Hirose S, Toki S, Miyao M and Matsuoka M (1999) High-level expression of maize phosphoenolpyruvate carboxylase in transgenic rice plants. Nat Biotechnol 17: 76–80.

Leegood R C, Lea P J, Adcock M D and Haeusler R E (1995) The regulation and control of photorespiration. Journal of Experimental Botany 46: 1397–1414.

Lipka V, Hausler R E, Rademacher T, Li J, Hirsch H J and Kreuzaler F (1999) *Solanum tuberosum* double transgenic expressing phosphoenolpyruvate carboxylase and NADP-malic enzyme display reduced electron requirement for CO2 fixation. Plant Science. 144: 93–105.

Lord J M (1972) Glycolate oxidoreductase in *Escherichia coli*. Biochimica et Biophysica Acta 267: 227–237.

Matsuoka M, Furbank R T, Fukayama H and Miyao M (2001) Molecular engineering of $C_4$ photosynthesis. Annu Rev Plant Physio. Plant Mol Biol 52: 297–314.

Nelson E B and Tolbert N E (1970) Glycolate dehydrogenase in green algae. Archives of Biochemistry & Biophysics 141: 102–110.

Pellicer M T, Badia J, Aguilar J and Baldoma L (1996) glc locus of *Escherichia coli*: characterization of genes encoding the subunits of glycolate oxidase and the glc regulator protein. Journal of Bacteriology 178: 2051–2059.

Ramazanov Z and Cardenas J (1992) Involvement of photorespiration and glycolate pathway in carbonic anhydrase induction and inorganic carbon concentration in Chlamydomonas reinhardtii. Physiologia Plantarum 84: 502–508.

Reichel C, Mathur J, Eckes P, Langenkemper K, Koncz C, Schell J, Reiss B and Maas C (1996) Enhanced green fluorescence by the expression of an Aequorea victoria green fluorescent protein mutant in mono- and dicotyledonous plant cells. Proc. National Academy of Sciences USA 93: 5888–5893.

Reiskind J B, Madsen T V, Van Ginkel L C and Bowes G (1997) Evidence that inducible C₄-type photosynthesis is a chloroplastic CO₂-concentrating mechanism in *Hydrilla*, a submersed monocot. Plant Cell Environ 20: 211–220.

Rumsby G and Cregeen D P (1999) Identification and expression of a cDNA for human hydroxypyruvate/glyoxylate reductase. Biochimica et Biophysica Acta 1446: 383–388.

Schell J, Kaulen H, Kreuzaler F, Eckes P, Rosahl S, Willmitzer L, Spena A, Baker B, Herrera-Estrella L and Fedoroff N (1985) Transfer and regulation of expression of chimeric genes in plants. Cold Spring Harb Symp Quant Biol 50: 421–431.

Suzuki S, Murai N, Burnell James N and Arai M (2000) Changes in photosynthetic carbon flow in transgenic rice plants that express C4-type phosphoenolpyruvate carboxykinase from Urochloa panicoides. Plant Physiology 124: 163–172.

Tolbert N E (1997) The CO₂ oxidative photosynthetic carbon cycle. Annu Rev Plant Physiol Plant Mol Biol 48: 1–25.

We claim:

1. A method for producing $C_3$ plants with suppressed photorespiration and improved $CO_2$ fixation, the method comprising introducing into a $C_3$ plant cell, a $C_3$ plant tissue or a $C_3$ plant one or more nucleic acid sequences, each incorporated into nuclear genomic or chloroplastic DNA by transformation, wherein said one or more nucleic acid sequences encode polypeptides having the enzymatic activities of (i) an enzyme selected from the group consisting of glycolate oxidase and glycolate dehydrogenase, (ii) glyoxylate carboligase and (iii) tartronic semialdehyde reductase, wherein said introduction results in de novo expression of polypeptides having the enzymatic activities of (i) an enzyme selected from the group consisting of glycolate oxidase and glycolate dehydrogenase, (ii) glyoxylate carboligase and (iii) tartronic semialdehyde reductase and wherein said polypeptides are localized in chloroplasts of the plant produced.

2. The method of claim 1 wherein each of said polypeptides comprises an amino acid sequence, that targets the polypeptide to the chloroplast.

3. The method of claim 1 wherein said polypeptides having the enzymatic activity of a glycolate oxidase are derived from the E. coli glc operon.

4. The method of claim 3 wherein said polypeptides comprise the amino acid sequences of SEQ ID NOS:2, 4 and 6.

5. The method of claim 1 wherein said one or more nucleic acid sequences comprise the polynucleotide sequences of SEQ ID NOS:1, 3 and 5.

6. The method of claim 1 wherein the polypeptide having the enzymatic activity of a glycolate dehydrogenase is a human glyoxylate reductase.

7. The method of claim 6 wherein said polypeptide comprises the amino acid sequence of SEQ ID NO:8.

8. The method of claim 1 wherein said one or more nucleic acid sequences comprise the polynucleotide sequence of SEQ ID NO:7.

9. The method of claim 1 wherein the polypeptide having the enzymatic activity of a glyoxylate carboligase is derived from E. coli.

10. The method of claim 9 wherein said polypeptide comprises the amino acid sequence of SEQ ID NO: 12.

11. The method of claim 1 wherein said one or more nucleic acid sequences comprise the polynucleotide sequence of SEQ ID NO: 11.

12. The method of claim 1 wherein the polypeptide having the enzymatic activity of a tartronic semialdehyde reductase is derived from E. coli.

13. The method of claim 12 wherein said polypeptide comprises the amino acid sequence of SEQ ID NO: 14.

14. The method of claim 1 wherein said one or more nucleic acid sequences comprise the polynucleotide sequence of SEQ ID NO: 13.

15. An isolated $C_3$ plant cell, $C_3$ plant tissue or $C_3$ plant comprising one or more transgenic nucleic acid sequences encoding polypeptides having the enzymatic activities of (i) an enzyme selected from the group consisting of glycolate oxidase and glycolate dehydrogenase, (ii) glyoxylate carboligase and (iii) tartronic semialdehyde reductase.

16. The plant cell, plant tissue or plant of claim 15 wherein each of said polypeptides comprises an amino acid sequence, and wherein each of said amino acid sequence targets said polypeptides to the chloroplast.

17. The plant cell, plant tissue or plant of claim 15 wherein the polypeptide having the enzymatic activity of a glycolate oxidase is derived from the E. coli glc operon.

18. The plant cell, plant tissue or plant of claim 17 wherein said polypeptides comprise the amino acid sequences of SEQ ID NOS:2, 4 and 6.

19. The plant cell, plant tissue or plant of claim 15 wherein said one or more nucleic acid sequences comprise the polynucleotide sequences of SEQ ID NOS:1, 3 and 5.

20. The plant cell, plant tissue or plant of claim 15 wherein the polypeptide having the enzymatic activity of a glycolate dehydrogenase is a human glyoxylate reductase.

21. The plant cell, plant tissue or plant of claim 20 wherein said polypeptide comprises the amino acid sequence of SEQ ID NO:8.

22. The plant cell, plant tissue or plant of claim 15 wherein said one or more nucleic acid sequences comprise the polynucleotide sequence of SEQ ID NO:7.

23. The plant cell, plant tissue or plant of claim 15 wherein the polypeptide having the enzymatic activity of a glyoxylate carboligase is derived from E. coli.

24. The plant cell, plant tissue or plant of claim 23 wherein said polypeptide comprises the amino acid sequence of SEQ ID NO: 12.

25. The plant cell, plant tissue or plant of claim 15 wherein said one or more nucleic acid sequences comprise the polynucleotide sequence of SEQ ID NO: 11.

26. The plant cell, plant tissue or plant of claim 15 wherein the polypeptide having the enzymatic activity of a tartronic semialdehyde reductase is derived from E. coli.

27. The plant cell, plant tissue or plant of claim 26 wherein said polypeptide comprises the amino acid sequence of SEQ ID NO: 14.

28. The plant cell, plant tissue or plant of claim 16 wherein said one or more nucleic acid sequences comprise the polynucleotide sequence of SEQ ID NO: 13.

29. A $C_3$ plant produced by the method of claim 1.

* * * * *

```
                         SEQUENCE LISTING

<160> NUMBER OF SEQ ID NOS: 14

<210> SEQ ID NO 1
<211> LENGTH: 1500
<212> TYPE: DNA
<213> ORGANISM: Escherichia coli
<220> FEATURE:
<221> NAME/KEY: CDS
<222> LOCATION: (1)..(1497)
<223> OTHER INFORMATION: glc D

<400> SEQUENCE: 1 atg agc atc ttg tac gaa gag cgt ctt gat ggc gct tta ccc gat gtc       48
Met Ser Ile Leu Tyr Glu Glu Arg Leu Asp Gly Ala Leu Pro Asp Val
1               5                   10                  15 gac cgc aca tcg gta ctg atg gca ctg cgt gag cat gtc cct gga ctt       96
Asp Arg Thr Ser Val Leu Met Ala Leu Arg Glu His Val Pro Gly Leu
                20                  25                  30 gag atc ctg cat acc gat gag gag atc att cct tac gag tgt gac ggg      144
Glu Ile Leu His Thr Asp Glu Glu Ile Ile Pro Tyr Glu Cys Asp Gly
            35                  40                  45 ttg agc gcg tat cgc acg cgt cca tta ctg gtt gtt ctg cct aag caa      192
Leu Ser Ala Tyr Arg Thr Arg Pro Leu Leu Val Val Leu Pro Lys Gln
        50                  55                  60 atg gaa cag gtg aca gcg att ctg gct gtc tgc cat cgc ctg cgt gta      240
Met Glu Gln Val Thr Ala Ile Leu Ala Val Cys His Arg Leu Arg Val
65                  70                  75                  80 ccg gtg gtg acc cgt ggt gca ggc acc ggg ctt tct ggt ggc gcg ctg      288
Pro Val Val Thr Arg Gly Ala Gly Thr Gly Leu Ser Gly Gly Ala Leu
                85                  90                  95 ccg ctg gaa aaa ggt gtg ttg gtg atg gcg cgc ttt aaa gag atc          336
Pro Leu Glu Lys Gly Val Leu Val Met Ala Arg Phe Lys Glu Ile
                100                 105                 110 ctc gac att aac ccc gtt ggt cgc cgc gcg cgc gtg cag cca ggc gtg      384
Leu Asp Ile Asn Pro Val Gly Arg Arg Ala Arg Val Gln Pro Gly Val
            115                 120                 125 cgt aac ctg gcg atc tcc cag gcc gtt gca ccg cat aat ctc tac tac      432
Arg Asn Leu Ala Ile Ser Gln Ala Val Ala Pro His Asn Leu Tyr Tyr
        130                 135                 140 gca ccg gac cct tcc tca caa atc gcc tgt tcc att ggc ggc aat gtg      480
Ala Pro Asp Pro Ser Ser Gln Ile Ala Cys Ser Ile Gly Gly Asn Val
145                 150                 155                 160 gct gaa aat gcc ggc ggc gtc cac tgc ctg aaa tat ggt ctg acc gta      528
Ala Glu Asn Ala Gly Gly Val His Cys Leu Lys Tyr Gly Leu Thr Val
                165                 170                 175 cat aac ctg ctg aaa att gaa gtg caa acg ctg gac ggc gag gca ctg      576
His Asn Leu Leu Lys Ile Glu Val Gln Thr Leu Asp Gly Glu Ala Leu
            180                 185                 190
```

-continued

| | | |
|---|---|---|
| aca ctt gga tcg gac gcg ctg gat tca cct ggt ttt gac ctg ctg gcg<br>Thr Leu Gly Ser Asp Ala Leu Asp Ser Pro Gly Phe Asp Leu Leu Ala<br>     195                  200                  205 | | 624 |
| ctg ttc acc gga tcg gaa ggt atg ctc ggc gtg acc acc gaa gtg acg<br>Leu Phe Thr Gly Ser Glu Gly Met Leu Gly Val Thr Thr Glu Val Thr<br> 210                     215                   220 | | 672 |
| gta aaa ctg ctg ccg aag ccg ccc gtg gcg cgg gtt ctg tta gcc agc<br>Val Lys Leu Leu Pro Lys Pro Pro Val Ala Arg Val Leu Leu Ala Ser<br>225                   230                   235                 240 | | 720 |
| ttt gac tcg gta gaa aaa gcc gga ctt gcg gtt ggt gac atc atc gcc<br>Phe Asp Ser Val Glu Lys Ala Gly Leu Ala Val Gly Asp Ile Ile Ala<br>             245                   250                   255 | | 768 |
| aat ggc att atc ccc ggc ggg ctg gag atg atg gat aac ctg tcg atc<br>Asn Gly Ile Ile Pro Gly Gly Leu Glu Met Met Asp Asn Leu Ser Ile<br>         260                   265                   270 | | 816 |
| cgc gcg gcg gaa gat ttt att cat gcc ggt tat ccc gtc gac gcc gaa<br>Arg Ala Ala Glu Asp Phe Ile His Ala Gly Tyr Pro Val Asp Ala Glu<br>             275                   280                   285 | | 864 |
| gcg att ttg tta tgc gag ctg gac ggc gtg gag tct gac gta cag gaa<br>Ala Ile Leu Leu Cys Glu Leu Asp Gly Val Glu Ser Asp Val Gln Glu<br>         290                   295                  300 | | 912 |
| gac tgc gag cgg gtt aac gac atc ttg ttg aaa gcg ggc gcg act gac<br>Asp Cys Glu Arg Val Asn Asp Ile Leu Leu Lys Ala Gly Ala Thr Asp<br>305                   310                   315                 320 | | 960 |
| gtc cgt ctg gca cag gac gaa gca gag cgt gta cgt ttc tgg gcc ggt<br>Val Arg Leu Ala Gln Asp Glu Ala Glu Arg Val Arg Phe Trp Ala Gly<br>             325                   330                   335 | | 1008 |
| cgc aaa aat gcg ttc ccg gcg gta gga cgt atc tcc ccg gat tac tac<br>Arg Lys Asn Ala Phe Pro Ala Val Gly Arg Ile Ser Pro Asp Tyr Tyr<br>                 340                   345                 350 | | 1056 |
| tgc atg gat ggc acc atc ccg cgt cgc gcc ctg cct ggc gta ctg gaa<br>Cys Met Asp Gly Thr Ile Pro Arg Arg Ala Leu Pro Gly Val Leu Glu<br>         355                   360                   365 | | 1104 |
| ggc att gcc cgt tta tcg cag caa tat gat tta cgt gtt gcc aac gtc<br>Gly Ile Ala Arg Leu Ser Gln Gln Tyr Asp Leu Arg Val Ala Asn Val<br>         370                   375                   380 | | 1152 |
| ttt cat gcc gga gat ggc aac atg cac ccg tta atc ctt ttc gat gcc<br>Phe His Ala Gly Asp Gly Asn Met His Pro Leu Ile Leu Phe Asp Ala<br>385                   390                   395                 400 | | 1200 |
| aac gaa ccc ggt gaa ttt gcc cgc gcg gaa gag ctg ggc ggg aag atc<br>Asn Glu Pro Gly Glu Phe Ala Arg Ala Glu Glu Leu Gly Gly Lys Ile<br>             405                   410                   415 | | 1248 |
| ctc gaa ctc tgc gtt gaa gtt ggc ggc agc atc agt ggc gaa cat ggc<br>Leu Glu Leu Cys Val Glu Val Gly Gly Ser Ile Ser Gly Glu His Gly<br>             420                   425                   430 | | 1296 |
| atc ggg cga gaa aaa atc aat caa atg tgc gcc cag ttc aac agc gat<br>Ile Gly Arg Glu Lys Ile Asn Gln Met Cys Ala Gln Phe Asn Ser Asp<br>         435                   440                   445 | | 1344 |
| gaa atc acg acc ttc cat gcg gtc aag gcg gcg ttt gac ccc gat ggt<br>Glu Ile Thr Thr Phe His Ala Val Lys Ala Ala Phe Asp Pro Asp Gly<br>450                   455                   460 | | 1392 |
| ttg ctg aac cct ggg aaa aac att ccc acg cta cac cgc tgt gct gaa<br>Leu Leu Asn Pro Gly Lys Asn Ile Pro Thr Leu His Arg Cys Ala Glu<br>465                   470                   475                 480 | | 1440 |
| ttt ggt gcc atg cat gtg cat cac ggt cat tta cct ttc cct gaa ctg<br>Phe Gly Ala Met His Val His His Gly His Leu Pro Phe Pro Glu Leu<br>                 485                   490                   495 | | 1488 |
| gag cgt ttc tga<br>Glu Arg Phe | | 1500 |

<210> SEQ ID NO 2
<211> LENGTH: 499
<212> TYPE: PRT
<213> ORGANISM: Escherichia coli

<400> SEQUENCE: 2

```
Met Ser Ile Leu Tyr Glu Glu Arg Leu Asp Gly Ala Leu Pro Asp Val
1               5                  10                  15

Asp Arg Thr Ser Val Leu Met Ala Leu Arg Glu His Val Pro Gly Leu
            20                  25                  30

Glu Ile Leu His Thr Asp Glu Glu Ile Ile Pro Tyr Glu Cys Asp Gly
        35                  40                  45

Leu Ser Ala Tyr Arg Thr Arg Pro Leu Leu Val Val Leu Pro Lys Gln
    50                  55                  60

Met Glu Gln Val Thr Ala Ile Leu Ala Val Cys His Arg Leu Arg Val
65                  70                  75                  80

Pro Val Val Thr Arg Gly Ala Gly Thr Gly Leu Ser Gly Gly Ala Leu
                85                  90                  95

Pro Leu Glu Lys Gly Val Leu Leu Val Met Ala Arg Phe Lys Glu Ile
            100                 105                 110

Leu Asp Ile Asn Pro Val Gly Arg Arg Ala Arg Val Gln Pro Gly Val
        115                 120                 125

Arg Asn Leu Ala Ile Ser Gln Ala Val Ala Pro His Asn Leu Tyr Tyr
    130                 135                 140

Ala Pro Asp Pro Ser Ser Gln Ile Ala Cys Ser Ile Gly Gly Asn Val
145                 150                 155                 160

Ala Glu Asn Ala Gly Gly Val His Cys Leu Lys Tyr Gly Leu Thr Val
                165                 170                 175

His Asn Leu Leu Lys Ile Glu Val Gln Thr Leu Asp Gly Glu Ala Leu
            180                 185                 190

Thr Leu Gly Ser Asp Ala Leu Asp Ser Pro Gly Phe Asp Leu Leu Ala
        195                 200                 205

Leu Phe Thr Gly Ser Glu Gly Met Leu Gly Val Thr Thr Glu Val Thr
    210                 215                 220

Val Lys Leu Leu Pro Lys Pro Val Ala Arg Val Leu Leu Ala Ser Phe
225                 230                 235                 240

Phe Asp Ser Val Glu Lys Ala Gly Leu Ala Val Gly Asp Ile Ile Ala
                245                 250                 255

Asn Gly Ile Ile Pro Gly Gly Leu Glu Met Met Asp Asn Leu Ser Ile
            260                 265                 270

Arg Ala Ala Glu Asp Phe Ile His Ala Gly Tyr Pro Val Asp Ala Glu
        275                 280                 285

Ala Ile Leu Leu Cys Glu Leu Asp Gly Val Glu Ser Asp Val Gln Glu
    290                 295                 300

Asp Cys Glu Arg Val Asn Asp Ile Leu Leu Lys Ala Gly Ala Thr Asp
305                 310                 315                 320

Val Arg Leu Ala Gln Asp Glu Ala Glu Arg Val Arg Phe Trp Ala Gly
                325                 330                 335

Arg Lys Asn Ala Phe Pro Ala Val Gly Arg Ile Ser Pro Asp Tyr Tyr
            340                 345                 350

Cys Met Asp Gly Thr Ile Pro Arg Arg Ala Leu Pro Gly Val Leu Glu
        355                 360                 365

Gly Ile Ala Arg Leu Ser Gln Gln Tyr Asp Leu Arg Val Ala Asn Val
    370                 375                 380
```

```
Phe His Ala Gly Asp Gly Asn Met His Pro Leu Ile Leu Phe Asp Ala
385                 390                 395                 400

Asn Glu Pro Gly Glu Phe Ala Arg Ala Glu Glu Leu Gly Gly Lys Ile
                405                 410                 415

Leu Glu Leu Cys Val Glu Val Gly Gly Ser Ile Ser Gly Glu His Gly
                420                 425                 430

Ile Gly Arg Glu Lys Ile Asn Gln Met Cys Ala Gln Phe Asn Ser Asp
            435                 440                 445

Glu Ile Thr Thr Phe His Ala Val Lys Ala Ala Phe Asp Pro Asp Gly
        450                 455                 460

Leu Leu Asn Pro Gly Lys Asn Ile Pro Thr Leu His Arg Cys Ala Glu
465                 470                 475                 480

Phe Gly Ala Met His Val His His Gly His Leu Pro Phe Pro Glu Leu
                485                 490                 495

Glu Arg Phe

<210> SEQ ID NO 3
<211> LENGTH: 1053
<212> TYPE: DNA
<213> ORGANISM: Escherichia coli
<220> FEATURE:
<221> NAME/KEY: CDS
<222> LOCATION: (1)..(1050)
<223> OTHER INFORMATION: glc E

<400> SEQUENCE: 3 atg cta cgc gag tgt gat tac agc cag gcg ctg ctg gag cag gtg aat      48
Met Leu Arg Glu Cys Asp Tyr Ser Gln Ala Leu Leu Glu Gln Val Asn
1               5                   10                  15 cag gcg att agc gat aaa acg ccg ctg gtg att cag ggc agc aat agc      96
Gln Ala Ile Ser Asp Lys Thr Pro Leu Val Ile Gln Gly Ser Asn Ser
            20                  25                  30 aaa gcc ttt tta ggt cgc cct gtc acc ggg caa acg ctg gat gtt cgt     144
Lys Ala Phe Leu Gly Arg Pro Val Thr Gly Gln Thr Leu Asp Val Arg
        35                  40                  45 tgt cat cgc ggc att gtt aat tac gac ccg acc gag ctg gtg ata acc     192
Cys His Arg Gly Ile Val Asn Tyr Asp Pro Thr Glu Leu Val Ile Thr
    50                  55                  60 gcg cgt gtc gga acg ccg ctg gtg aca att gaa gcg gcg ctg gaa agc     240
Ala Arg Val Gly Thr Pro Leu Val Thr Ile Glu Ala Ala Leu Glu Ser
65                  70                  75                  80 gcg ggg caa atg ctc ccc tgt gag ccg ccg cat tat ggt gaa gaa gcc     288
Ala Gly Gln Met Leu Pro Cys Glu Pro Pro His Tyr Gly Glu Glu Ala
                85                  90                  95 acc tgg ggc ggg atg gtc gcc tgc ggg ctg gcg ggg ccg cgt cgc ccg     336
Thr Trp Gly Gly Met Val Ala Cys Gly Leu Ala Gly Pro Arg Arg Pro
            100                 105                 110 tgg agc ggt tcg gtc cgc gat ttt gtc ctc ggc acg cgc atc att acc     384
Trp Ser Gly Ser Val Arg Asp Phe Val Leu Gly Thr Arg Ile Ile Thr
        115                 120                 125 ggc gct gga aaa cat ctg cgt ttt ggt ggc gaa gtg atg aaa aac gtt     432
Gly Ala Gly Lys His Leu Arg Phe Gly Gly Glu Val Met Lys Asn Val
    130                 135                 140 gcc gga tac gat ctc tca cgg tta atg gtc gga agc tac ggt tgt ctt     480
Ala Gly Tyr Asp Leu Ser Arg Leu Met Val Gly Ser Tyr Gly Cys Leu
145                 150                 155                 160 ggc gtg ctc act gaa atc tca atg aaa gtg tta ccg cga ccg cgc gcc     528
Gly Val Leu Thr Glu Ile Ser Met Lys Val Leu Pro Arg Pro Arg Ala
                165                 170                 175
```

```
tcc ctg agc ctg cgt cgg gaa atc agc ctg caa gaa gcc atg agt gaa      576
Ser Leu Ser Leu Arg Arg Glu Ile Ser Leu Gln Glu Ala Met Ser Glu
        180                 185                 190 atc gcc gag tgg caa ctc cag cca tta ccc att agt ggc tta tgt tac      624
Ile Ala Glu Trp Gln Leu Gln Pro Leu Pro Ile Ser Gly Leu Cys Tyr
            195                 200                 205 ttc gac aat gcg ttg tgg atc cgc ctt gag ggc ggc gaa gga tcg gta      672
Phe Asp Asn Ala Leu Trp Ile Arg Leu Glu Gly Gly Glu Gly Ser Val
        210                 215                 220 aaa gca gcg cgt gaa ctg ctg ggt ggc gaa gag gtt gcc ggt cag ttc      720
Lys Ala Arg Glu Leu Leu Gly Gly Glu Glu Val Ala Gly Gln Phe
225                 230                 235                 240 tgg cag caa ttg cgt gaa caa caa ctg ccg ttc ttc tcg tta cca ggt      768
Trp Gln Gln Leu Arg Glu Gln Gln Leu Pro Phe Phe Ser Leu Pro Gly
                245                 250                 255 acc tta tgg cgc att tca tta ccc agt gat gcg ccg atg atg gat tta      816
Thr Leu Trp Arg Ile Ser Leu Pro Ser Asp Ala Pro Met Met Asp Leu
            260                 265                 270 ccc ggc gag caa ctg atc gac tgg ggc ggg gcg tta cgc tgg ctg aaa      864
Pro Gly Glu Gln Leu Ile Asp Trp Gly Gly Ala Leu Arg Trp Leu Lys
        275                 280                 285 tcg aca gcc gag gac aat caa atc cat cgc atc gcc cgc aac gct ggc      912
Ser Thr Ala Glu Asp Asn Gln Ile His Arg Ile Ala Arg Asn Ala Gly
290                 295                 300 ggt cat gcg acc cgc ttt agt gcc gga gat ggt ggc ttt gcc ccg cta      960
Gly His Ala Thr Arg Phe Ser Ala Gly Asp Gly Gly Phe Ala Pro Leu
305                 310                 315                 320 tcg gct cct tta ttc cgc tat cac cag cag ctt aaa cag cag ctc gac     1008
Ser Ala Pro Leu Phe Arg Tyr His Gln Gln Leu Lys Gln Gln Leu Asp
                325                 330                 335 cct tgc ggc gtg ttt aac ccc ggt cgc atg tac gcg gaa ctt tga         1053
Pro Cys Gly Val Phe Asn Pro Gly Arg Met Tyr Ala Glu Leu
            340                 345                 350
```

<210> SEQ ID NO 4
<211> LENGTH: 350
<212> TYPE: PRT
<213> ORGANISM: Escherichia coli

<400> SEQUENCE: 4

```
Met Leu Arg Glu Cys Asp Tyr Ser Gln Ala Leu Leu Glu Gln Val Asn
1               5                   10                  15

Gln Ala Ile Ser Asp Lys Thr Pro Leu Val Ile Gln Gly Ser Asn Ser
            20                  25                  30

Lys Ala Phe Leu Gly Arg Pro Val Thr Gly Gln Thr Leu Asp Val Arg
        35                  40                  45

Cys His Arg Gly Ile Val Asn Tyr Asp Pro Thr Glu Leu Val Ile Thr
    50                  55                  60

Ala Arg Val Gly Thr Pro Leu Val Thr Ile Glu Ala Ala Leu Glu Ser
65                  70                  75                  80

Ala Gly Gln Met Leu Pro Cys Glu Pro Pro His Tyr Gly Glu Glu Ala
                85                  90                  95

Thr Trp Gly Gly Met Val Ala Cys Gly Leu Ala Gly Pro Arg Arg Pro
            100                 105                 110

Trp Ser Gly Ser Val Arg Asp Phe Val Leu Gly Thr Arg Ile Ile Thr
        115                 120                 125

Gly Ala Gly Lys His Leu Arg Phe Gly Gly Glu Val Met Lys Asn Val
    130                 135                 140
```

```
Ala Gly Tyr Asp Leu Ser Arg Leu Met Val Gly Ser Tyr Gly Cys Leu
145                 150                 155                 160

Gly Val Leu Thr Glu Ile Ser Met Lys Val Leu Pro Arg Pro Arg Ala
                165                 170                 175

Ser Leu Ser Leu Arg Arg Glu Ile Ser Leu Gln Glu Ala Met Ser Glu
            180                 185                 190

Ile Ala Glu Trp Gln Leu Gln Pro Leu Pro Ile Ser Gly Leu Cys Tyr
        195                 200                 205

Phe Asp Asn Ala Leu Trp Ile Arg Leu Glu Gly Gly Glu Gly Ser Val
    210                 215                 220

Lys Ala Ala Arg Glu Leu Leu Gly Gly Glu Glu Val Ala Gly Gln Phe
225                 230                 235                 240

Trp Gln Gln Leu Arg Glu Gln Gln Leu Pro Phe Phe Ser Leu Pro Gly
                245                 250                 255

Thr Leu Trp Arg Ile Ser Leu Pro Ser Asp Ala Pro Met Met Asp Leu
            260                 265                 270

Pro Gly Glu Gln Leu Ile Asp Trp Gly Gly Ala Leu Arg Trp Leu Lys
        275                 280                 285

Ser Thr Ala Glu Asp Asn Gln Ile His Arg Ile Ala Arg Asn Ala Gly
290                 295                 300

Gly His Ala Thr Arg Phe Ser Ala Gly Asp Gly Phe Ala Pro Leu
305                 310                 315                 320

Ser Ala Pro Leu Phe Arg Tyr His Gln Gln Leu Lys Gln Gln Leu Asp
                325                 330                 335

Pro Cys Gly Val Phe Asn Pro Gly Arg Met Tyr Ala Glu Leu
            340                 345                 350

<210> SEQ ID NO 5
<211> LENGTH: 1224
<212> TYPE: DNA
<213> ORGANISM: Escherichia coli
<220> FEATURE:
<221> NAME/KEY: CDS
<222> LOCATION: (1)..(1221)
<223> OTHER INFORMATION: glc F

<400> SEQUENCE: 5 atg caa acc caa tta act gaa gag atg cgg cag aac gcg cgc gcg ctg      48
Met Gln Thr Gln Leu Thr Glu Glu Met Arg Gln Asn Ala Arg Ala Leu
1               5                   10                  15 gaa gcc gac agc atc ctg cgc gcc tgt gtt cac tgc gga ttt tgt acc      96
Glu Ala Asp Ser Ile Leu Arg Ala Cys Val His Cys Gly Phe Cys Thr
            20                  25                  30 gca acc tgc cca acc tat cag ctt ctg ggc gat gaa ctg gac ggg ccg     144
Ala Thr Cys Pro Thr Tyr Gln Leu Leu Gly Asp Glu Leu Asp Gly Pro
        35                  40                  45 cgc ggg cgc atc tat ctg att aaa cag gtg ctg gaa ggc aac gaa gtc     192
Arg Gly Arg Ile Tyr Leu Ile Lys Gln Val Leu Glu Gly Asn Glu Val
    50                  55                  60 acg ctt aaa aca cag gag cat ctc gat cgc tgc ctc act tgc cgt aat     240
Thr Leu Lys Thr Gln Glu His Leu Asp Arg Cys Leu Thr Cys Arg Asn
65                  70                  75                  80 tgt gaa acc acc tgt cct tct ggt gtg cgc tat cac aat ttg ctg gat     288
Cys Glu Thr Thr Cys Pro Ser Gly Val Arg Tyr His Asn Leu Leu Asp
                85                  90                  95 atc ggg cgt gat att gtc gag cag aaa gtg aaa cgc cca ctg ccg gag     336
Ile Gly Arg Asp Ile Val Glu Gln Lys Val Lys Arg Pro Leu Pro Glu
            100                 105                 110
```

-continued

```
cga ata ctg cgc gaa gga ttg cgc cag gta gtg ccg cgt ccg gcg gtc      384
Arg Ile Leu Arg Glu Gly Leu Arg Gln Val Val Pro Arg Pro Ala Val
        115                 120                 125 ttc cgt gcg ctg acg cag gta ggg ctg gtg ctg cga ccg ttt tta ccg      432
Phe Arg Ala Leu Thr Gln Val Gly Leu Val Leu Arg Pro Phe Leu Pro
130                 135                 140 gaa cag gtc aga gca aaa ctg cct gct gaa acg gtg aaa gct aaa ccg      480
Glu Gln Val Arg Ala Lys Leu Pro Ala Glu Thr Val Lys Ala Lys Pro
145                 150                 155                 160 cgt ccg ccg ctg cgc cat aag cgt cgg gtt tta atg ttg gaa ggc tgc      528
Arg Pro Pro Leu Arg His Lys Arg Arg Val Leu Met Leu Glu Gly Cys
                165                 170                 175 gcc cag cct acg ctt tcg ccc aac acc aac gcg gca act gcg cga gtg      576
Ala Gln Pro Thr Leu Ser Pro Asn Thr Asn Ala Ala Thr Ala Arg Val
            180                 185                 190 ctg gat cgt ctg ggg atc agc gtc atg cca gct aac gaa gca ggc tgt      624
Leu Asp Arg Leu Gly Ile Ser Val Met Pro Ala Asn Glu Ala Gly Cys
        195                 200                 205 tgt ggc gcg gtg gac tat cat ctt aat gcg cag gag aaa ggg ctg gca      672
Cys Gly Ala Val Asp Tyr His Leu Asn Ala Gln Glu Lys Gly Leu Ala
210                 215                 220 cgg gcg cgc aat aat att gat gcc tgg tgg ccc gcg att gaa gca ggt      720
Arg Ala Arg Asn Asn Ile Asp Ala Trp Trp Pro Ala Ile Glu Ala Gly
225                 230                 235                 240 gcc gag gca att ttg caa acc gcc agc ggc tgc ggc gcg ttt gtc aaa      768
Ala Glu Ala Ile Leu Gln Thr Ala Ser Gly Cys Gly Ala Phe Val Lys
                245                 250                 255 gag tat ggg cag atg ctg aaa aac gat gcg tta tat gcc gat aaa gca      816
Glu Tyr Gly Gln Met Leu Lys Asn Asp Ala Leu Tyr Ala Asp Lys Ala
            260                 265                 270 cgt cag gtc agt gaa ctg gcg gtc gat tta gtc gaa ctt ctg cgc gag      864
Arg Gln Val Ser Glu Leu Ala Val Asp Leu Val Glu Leu Leu Arg Glu
        275                 280                 285 gaa ccg ctg gaa aaa ctg gca att cgc ggc gat aaa aag ctg gcc ttc      912
Glu Pro Leu Glu Lys Leu Ala Ile Arg Gly Asp Lys Lys Leu Ala Phe
290                 295                 300 cac tgt ccg tgt acc cta caa cat gcg caa aag ctg aac ggc gaa gtg      960
His Cys Pro Cys Thr Leu Gln His Ala Gln Lys Leu Asn Gly Glu Val
305                 310                 315                 320 gaa aaa gtg ttg ctt cgt ctt gga ttt acc tta acg gac gtt ccc gac     1008
Glu Lys Val Leu Leu Arg Leu Gly Phe Thr Leu Thr Asp Val Pro Asp
                325                 330                 335 agc cat ctg tgc tgc ggt tca gcg gga aca tat gcg tta acg cat ccc     1056
Ser His Leu Cys Cys Gly Ser Ala Gly Thr Tyr Ala Leu Thr His Pro
            340                 345                 350 gat ctg gca cgc cag ctg cgg gat aac aaa atg aat gcg ctg gaa agc     1104
Asp Leu Ala Arg Gln Leu Arg Asp Asn Lys Met Asn Ala Leu Glu Ser
        355                 360                 365 ggc aaa ccg gaa atg atc gtc acc gcc aac att ggt tgc cag acg cat     1152
Gly Lys Pro Glu Met Ile Val Thr Ala Asn Ile Gly Cys Gln Thr His
370                 375                 380 ctg gcg agc gcc ggt cgt acc tct gtg cgt cac tgg att gaa att gta     1200
Leu Ala Ser Ala Gly Arg Thr Ser Val Arg His Trp Ile Glu Ile Val
385                 390                 395                 400 gaa caa gcc ctt gaa aag gaa taa                                     1224
Glu Gln Ala Leu Glu Lys Glu
                405
```

<210> SEQ ID NO 6

<211> LENGTH: 407
<212> TYPE: PRT
<213> ORGANISM: Escherichia coli

<400> SEQUENCE: 6

```
Met Gln Thr Gln Leu Thr Glu Glu Met Arg Gln Asn Ala Arg Ala Leu
1               5                   10                  15

Glu Ala Asp Ser Ile Leu Arg Ala Cys Val His Cys Gly Phe Cys Thr
            20                  25                  30

Ala Thr Cys Pro Thr Tyr Gln Leu Leu Gly Asp Glu Leu Asp Gly Pro
        35                  40                  45

Arg Gly Arg Ile Tyr Leu Ile Lys Gln Val Leu Glu Gly Asn Glu Val
    50                  55                  60

Thr Leu Lys Thr Gln Glu His Leu Asp Arg Cys Leu Thr Cys Arg Asn
65                  70                  75                  80

Cys Glu Thr Thr Cys Pro Ser Gly Val Arg Tyr His Asn Leu Leu Asp
                85                  90                  95

Ile Gly Arg Asp Ile Val Glu Gln Lys Val Lys Arg Pro Leu Pro Glu
            100                 105                 110

Arg Ile Leu Arg Glu Gly Leu Arg Gln Val Val Pro Arg Pro Ala Val
        115                 120                 125

Phe Arg Ala Leu Thr Gln Val Gly Leu Val Leu Arg Pro Phe Leu Pro
130                 135                 140

Glu Gln Val Arg Ala Lys Leu Pro Ala Glu Thr Val Lys Ala Lys Pro
145                 150                 155                 160

Arg Pro Pro Leu Arg His Lys Arg Arg Val Leu Met Leu Glu Gly Cys
                165                 170                 175

Ala Gln Pro Thr Leu Ser Pro Asn Thr Asn Ala Ala Thr Ala Arg Val
            180                 185                 190

Leu Asp Arg Leu Gly Ile Ser Val Met Pro Ala Asn Glu Ala Gly Cys
        195                 200                 205

Cys Gly Ala Val Asp Tyr His Leu Asn Ala Gln Glu Lys Gly Leu Ala
    210                 215                 220

Arg Ala Arg Asn Asn Ile Asp Ala Trp Trp Pro Ala Ile Glu Ala Gly
225                 230                 235                 240

Ala Glu Ala Ile Leu Gln Thr Ala Ser Gly Cys Gly Ala Phe Val Lys
                245                 250                 255

Glu Tyr Gly Gln Met Leu Lys Asn Asp Ala Leu Tyr Ala Asp Lys Ala
            260                 265                 270

Arg Gln Val Ser Glu Leu Ala Val Asp Leu Val Glu Leu Leu Arg Glu
        275                 280                 285

Glu Pro Leu Glu Lys Leu Ala Ile Arg Gly Asp Lys Lys Leu Ala Phe
    290                 295                 300

His Cys Pro Cys Thr Leu Gln His Ala Gln Lys Leu Asn Gly Glu Val
305                 310                 315                 320

Glu Lys Val Leu Leu Arg Leu Gly Phe Thr Leu Thr Asp Val Pro Asp
                325                 330                 335

Ser His Leu Cys Cys Gly Ser Ala Gly Thr Tyr Ala Leu Thr His Pro
            340                 345                 350

Asp Leu Ala Arg Gln Leu Arg Asp Asn Lys Met Asn Ala Leu Glu Ser
        355                 360                 365

Gly Lys Pro Glu Met Ile Val Thr Ala Asn Ile Gly Cys Gln Thr His
    370                 375                 380

Leu Ala Ser Ala Gly Arg Thr Ser Val Arg His Trp Ile Glu Ile Val
```

-continued

```
                385                 390                 395                 400
            Glu Gln Ala Leu Glu Lys Glu
                            405

<210> SEQ ID NO 7
<211> LENGTH: 987
<212> TYPE: DNA
<213> ORGANISM: Homo sapiens
<220> FEATURE:
<221> NAME/KEY: CDS
<222> LOCATION: (1)..(984)
<223> OTHER INFORMATION: Glyoxylate Reductase

<400> SEQUENCE: 7 atg aga ccg gtg cga ctc atg aag gtg ttc gtc acc cgc agg ata ccc        48
Met Arg Pro Val Arg Leu Met Lys Val Phe Val Thr Arg Arg Ile Pro
1               5                   10                  15 gcc gag ggt agg gtc gcg ctc gcc cgg gcg gca gac tgt gag gtg gag        96
Ala Glu Gly Arg Val Ala Leu Ala Arg Ala Ala Asp Cys Glu Val Glu
            20                  25                  30 cag tgg gac tcg gat gag ccc atc cct gcc aag gag cta gag cga ggt       144
Gln Trp Asp Ser Asp Glu Pro Ile Pro Ala Lys Glu Leu Glu Arg Gly
        35                  40                  45 gtg gcg ggg gcc cac ggc ctg ctc tgc ctc ctc tcc gac cac gtg gac       192
Val Ala Gly Ala His Gly Leu Leu Cys Leu Leu Ser Asp His Val Asp
    50                  55                  60 aag agg atc ctg gat gct gca ggg gcc aat ctc aaa gtc atc agc acc       240
Lys Arg Ile Leu Asp Ala Ala Gly Ala Asn Leu Lys Val Ile Ser Thr
65                  70                  75                  80 atg tct gtg ggc atc gac cac ttg gct ttg gat gaa atc aag aag cgt       288
Met Ser Val Gly Ile Asp His Leu Ala Leu Asp Glu Ile Lys Lys Arg
                85                  90                  95 ggg atc cga gtt ggc tac acc cca gat gtc ctg aca gat acc acc gcc       336
Gly Ile Arg Val Gly Tyr Thr Pro Asp Val Leu Thr Asp Thr Thr Ala
            100                 105                 110 gaa ctc gca gtc tcc ctg cta ctt acc acc tgc cgc cgg ttg ccg gag       384
Glu Leu Ala Val Ser Leu Leu Leu Thr Thr Cys Arg Arg Leu Pro Glu
        115                 120                 125 gcc atc gag gaa gtg aag aat ggt ggc tgg acc tcg tgg aag ccc ctc       432
Ala Ile Glu Glu Val Lys Asn Gly Gly Trp Thr Ser Trp Lys Pro Leu
    130                 135                 140 tgg ctg tgt ggc tat gga ctc acg cag agc act gtc ggc atc atc ggg       480
Trp Leu Cys Gly Tyr Gly Leu Thr Gln Ser Thr Val Gly Ile Ile Gly
145                 150                 155                 160 ctg ggg cgc ata ggc cag gcc att gct cgg cgt ctg aaa cca ttc ggt       528
Leu Gly Arg Ile Gly Gln Ala Ile Ala Arg Arg Leu Lys Pro Phe Gly
                165                 170                 175 gtc cag aga ttt ctg tac aca ggg cgc cag ccc agg cct gag gaa gca       576
Val Gln Arg Phe Leu Tyr Thr Gly Arg Gln Pro Arg Pro Glu Glu Ala
            180                 185                 190 gca gaa ttc cag gca gag ttt gtg tct acc cct gag ctg gct gcc caa       624
Ala Glu Phe Gln Ala Glu Phe Val Ser Thr Pro Glu Leu Ala Ala Gln
        195                 200                 205 tct gat ttc atc gtc gtg gcc tgc tcc tta aca cct gca acc gag gga       672
Ser Asp Phe Ile Val Val Ala Cys Ser Leu Thr Pro Ala Thr Glu Gly
    210                 215                 220 ctc tgc aac aag gac ttc ttc cag aag atg aag gaa aca gct gtg ttc       720
Leu Cys Asn Lys Asp Phe Phe Gln Lys Met Lys Glu Thr Ala Val Phe
225                 230                 235                 240 atc aac atc agc agg ggc gac gtc gta aac cag gac gac ctg tac cag       768
Ile Asn Ile Ser Arg Gly Asp Val Val Asn Gln Asp Asp Leu Tyr Gln
```

-continued

```
                    245                 250                 255
gcc ttg gcc agt ggt aag att gca gct gct gga ctg gat gtg acg agc      816
Ala Leu Ala Ser Gly Lys Ile Ala Ala Ala Gly Leu Asp Val Thr Ser
            260                 265                 270 cca gaa cca ctg cct aca aac cac cct ctc ctg acc ctg aag aac tgt      864
Pro Glu Pro Leu Pro Thr Asn His Pro Leu Leu Thr Leu Lys Asn Cys
        275                 280                 285 gtg att ctg ccc cac att ggc agt gcc acc cac aga acc cgc aac acc      912
Val Ile Leu Pro His Ile Gly Ser Ala Thr His Arg Thr Arg Asn Thr
    290                 295                 300 atg tcc ttg ttg gca gct aac aac ttg ctg gct ggc ctg aga ggg gag      960
Met Ser Leu Leu Ala Ala Asn Asn Leu Leu Ala Gly Leu Arg Gly Glu
305                 310                 315                 320 ccg atg cct agt gaa ctc aag ctg tag                                  987
Pro Met Pro Ser Glu Leu Lys Leu
                325
```

<210> SEQ ID NO 8
<211> LENGTH: 328
<212> TYPE: PRT
<213> ORGANISM: Homo sapiens

<400> SEQUENCE: 8

```
Met Arg Pro Val Arg Leu Met Lys Val Phe Val Thr Arg Arg Ile Pro
1               5                   10                  15

Ala Glu Gly Arg Val Ala Leu Ala Arg Ala Ala Asp Cys Glu Val Glu
            20                  25                  30

Gln Trp Asp Ser Asp Glu Pro Ile Pro Ala Lys Glu Leu Glu Arg Gly
        35                  40                  45

Val Ala Gly Ala His Gly Leu Leu Cys Leu Leu Ser Asp His Val Asp
    50                  55                  60

Lys Arg Ile Leu Asp Ala Ala Gly Ala Asn Leu Lys Val Ile Ser Thr
65                  70                  75                  80

Met Ser Val Gly Ile Asp His Leu Ala Leu Asp Glu Ile Lys Lys Arg
                85                  90                  95

Gly Ile Arg Val Gly Tyr Thr Pro Asp Val Leu Thr Asp Thr Thr Ala
            100                 105                 110

Glu Leu Ala Val Ser Leu Leu Leu Thr Thr Cys Arg Arg Leu Pro Glu
        115                 120                 125

Ala Ile Glu Glu Val Lys Asn Gly Gly Trp Thr Ser Trp Lys Pro Leu
    130                 135                 140

Trp Leu Cys Gly Tyr Gly Leu Thr Gln Ser Thr Val Gly Ile Ile Gly
145                 150                 155                 160

Leu Gly Arg Ile Gly Gln Ala Ile Ala Arg Arg Leu Lys Pro Phe Gly
                165                 170                 175

Val Gln Arg Phe Leu Tyr Thr Gly Arg Gln Pro Arg Pro Glu Glu Ala
            180                 185                 190

Ala Glu Phe Gln Ala Glu Phe Val Ser Thr Pro Glu Leu Ala Ala Gln
        195                 200                 205

Ser Asp Phe Ile Val Val Ala Cys Ser Leu Thr Pro Ala Thr Glu Gly
    210                 215                 220

Leu Cys Asn Lys Asp Phe Phe Gln Lys Met Lys Glu Thr Ala Val Phe
225                 230                 235                 240

Ile Asn Ile Ser Arg Gly Asp Val Val Asn Gln Asp Asp Leu Tyr Gln
                245                 250                 255

Ala Leu Ala Ser Gly Lys Ile Ala Ala Ala Gly Leu Asp Val Thr Ser
```

```
                  260            265            270
Pro Glu Pro Leu Pro Thr Asn His Pro Leu Leu Thr Leu Lys Asn Cys
            275                280                285

Val Ile Leu Pro His Ile Gly Ser Ala Thr His Arg Thr Arg Asn Thr
        290                295                300

Met Ser Leu Leu Ala Ala Asn Asn Leu Leu Ala Gly Leu Arg Gly Glu
305                310                315                320

Pro Met Pro Ser Glu Leu Lys Leu
                325

<210> SEQ ID NO 9
<211> LENGTH: 1704
<212> TYPE: DNA
<213> ORGANISM: Arabidopsis thaliana
<220> FEATURE:
<221> NAME/KEY: CDS
<222> LOCATION: (1)..(1701)
<223> OTHER INFORMATION: E. coli glc operon homologue

<400> SEQUENCE: 9 atg gct ttc gct tca aaa ttc gct cgt tct aaa act att ctc tct ttt        48
Met Ala Phe Ala Ser Lys Phe Ala Arg Ser Lys Thr Ile Leu Ser Phe
1               5                  10                  15 ctc cgg cct tgt cgt cag ctc cac tcg acg ccc aag tca acc ggt gac        96
Leu Arg Pro Cys Arg Gln Leu His Ser Thr Pro Lys Ser Thr Gly Asp
                20                  25                  30 gtg acc gta ctt tct ccg gtg aag gga cgc cgg aga ctt cca act tgc       144
Val Thr Val Leu Ser Pro Val Lys Gly Arg Arg Arg Leu Pro Thr Cys
            35                  40                  45 tgg tcg agc tct ctg ttc cca ttg gcg ata gct gcc tcc gcc act tct       192
Trp Ser Ser Ser Leu Phe Pro Leu Ala Ile Ala Ala Ser Ala Thr Ser
        50                  55                  60 ttc gct tac ctg aat ctg tcg aat cct tct atc agt gaa tca tca tcg       240
Phe Ala Tyr Leu Asn Leu Ser Asn Pro Ser Ile Ser Glu Ser Ser Ser
65                  70                  75                  80 gct ttg gat tca aga gat ata act gtt ggt gga aaa gat agc act gaa       288
Ala Leu Asp Ser Arg Asp Ile Thr Val Gly Gly Lys Asp Ser Thr Glu
                85                  90                  95 gct gtt gtt aaa gga gaa tac aaa caa gtc cct aag gag ctt att tct       336
Ala Val Val Lys Gly Glu Tyr Lys Gln Val Pro Lys Glu Leu Ile Ser
                100                 105                 110 caa ttg aaa act atc ctc gag gat aac ttg aca act gac tac gat gag       384
Gln Leu Lys Thr Ile Leu Glu Asp Asn Leu Thr Thr Asp Tyr Asp Glu
            115                 120                 125 agg tac ttc cat ggg aag ccc cag aac agt ttt cac aag gca gtc aac       432
Arg Tyr Phe His Gly Lys Pro Gln Asn Ser Phe His Lys Ala Val Asn
        130                 135                 140 att cct gat gtc gtt gtt ttc cct agg tcc gaa gaa gaa gtc tcc aag       480
Ile Pro Asp Val Val Val Phe Pro Arg Ser Glu Glu Glu Val Ser Lys
145                 150                 155                 160 att ctt aaa tcc tgc aat gaa tat aag gtt cct att gta cca tat ggt       528
Ile Leu Lys Ser Cys Asn Glu Tyr Lys Val Pro Ile Val Pro Tyr Gly
                165                 170                 175 ggg gca aca tcg atc gag ggt cat acc ctt gct cca aaa gga ggt gtg       576
Gly Ala Thr Ser Ile Glu Gly His Thr Leu Ala Pro Lys Gly Gly Val
                180                 185                 190 tgc att gac atg tca tta atg aag agg gtg aaa gca tta cat gtg gag       624
Cys Ile Asp Met Ser Leu Met Lys Arg Val Lys Ala Leu His Val Glu
            195                 200                 205 gat atg gat gtt att gtt gag cct gga att ggt tgg ctg gag ctt aat       672
Asp Met Asp Val Ile Val Glu Pro Gly Ile Gly Trp Leu Glu Leu Asn
```

```
                Asp Met Asp Val Ile Val Glu Pro Gly Ile Gly Trp Leu Glu Leu Asn
                    210                 215                 220 gaa tat ttg gaa gag tat ggt cta ttc ttt cct ctt gat cca gga cct          720
Glu Tyr Leu Glu Glu Tyr Gly Leu Phe Phe Pro Leu Asp Pro Gly Pro
225                 230                 235                 240 ggt gcc tcc ata gga ggc atg tgt gct acg cgt tgc tct ggc tct tta          768
Gly Ala Ser Ile Gly Gly Met Cys Ala Thr Arg Cys Ser Gly Ser Leu
                245                 250                 255 gct gta agg tat gga act atg cgt gac aat gtt ata agc ctc aag gtg          816
Ala Val Arg Tyr Gly Thr Met Arg Asp Asn Val Ile Ser Leu Lys Val
                260                 265                 270 gtt ctt cct aat gga gat gtt gtg aag aca gct tca cgt gcc aga aag          864
Val Leu Pro Asn Gly Asp Val Val Lys Thr Ala Ser Arg Ala Arg Lys
                275                 280                 285 agt gct gct gga tac gat ttg act cgc ttg ata att ggg agt gag ggt          912
Ser Ala Ala Gly Tyr Asp Leu Thr Arg Leu Ile Ile Gly Ser Glu Gly
                290                 295                 300 act tta gga gtc att act gag att act ctc cga ctt cag aaa atc cca          960
Thr Leu Gly Val Ile Thr Glu Ile Thr Leu Arg Leu Gln Lys Ile Pro
305                 310                 315                 320 cag cat tca gtg gtg gca gtt tgc aat ttc cct aca gtt aag gat gct         1008
Gln His Ser Val Val Ala Val Cys Asn Phe Pro Thr Val Lys Asp Ala
                325                 330                 335 gca gac gtg gcc att gcc act atg atg tct gga ata cag gtg tca aga         1056
Ala Asp Val Ala Ile Ala Thr Met Met Ser Gly Ile Gln Val Ser Arg
                340                 345                 350 gtg gaa ctc ctt gac gag gtt caa atc aga gct att aat atg gca aac         1104
Val Glu Leu Leu Asp Glu Val Gln Ile Arg Ala Ile Asn Met Ala Asn
                355                 360                 365 ggg aaa aat ttg act gaa gct cca act ctg atg ttc gag ttt ata gga         1152
Gly Lys Asn Leu Thr Glu Ala Pro Thr Leu Met Phe Glu Phe Ile Gly
                370                 375                 380 aca gag gca tat aca cgt gag cag acg caa att gtt cag caa att gct         1200
Thr Glu Ala Tyr Thr Arg Glu Gln Thr Gln Ile Val Gln Gln Ile Ala
385                 390                 395                 400 tcc aaa cac aat gga tca gac ttt atg ttc gca gaa gaa cct gaa gca         1248
Ser Lys His Asn Gly Ser Asp Phe Met Phe Ala Glu Glu Pro Glu Ala
                405                 410                 415 aaa aaa gaa ctc tgg aag ata aga aaa gag gcg ctg tgg gct tgc tat         1296
Lys Lys Glu Leu Trp Lys Ile Arg Lys Glu Ala Leu Trp Ala Cys Tyr
                420                 425                 430 gct atg gcg cca ggt cat gaa gca atg att aca gat gtc tgt gtc cct         1344
Ala Met Ala Pro Gly His Glu Ala Met Ile Thr Asp Val Cys Val Pro
                435                 440                 445 tta tct cac ctt gca gaa ctc ata tca aga tcc aaa aaa gag ctt gat         1392
Leu Ser His Leu Ala Glu Leu Ile Ser Arg Ser Lys Lys Glu Leu Asp
                450                 455                 460 gca tca tcg ttg ttg tgt acc gtt att gct cat gcc gga gat gga aac         1440
Ala Ser Ser Leu Leu Cys Thr Val Ile Ala His Ala Gly Asp Gly Asn
465                 470                 475                 480 ttt cac aca tgt att atg ttt gat cca agc agt gaa gag cag aga aga         1488
Phe His Thr Cys Ile Met Phe Asp Pro Ser Ser Glu Glu Gln Arg Arg
                485                 490                 495 gaa gca gaa aga ctg aac cac ttt atg gtt cac agt gca ctg tcc atg         1536
Glu Ala Glu Arg Leu Asn His Phe Met Val His Ser Ala Leu Ser Met
                500                 505                 510 gat gga aca tgt act gga gaa cac ggt gtt gga aca gga aaa atg aag         1584
Asp Gly Thr Cys Thr Gly Glu His Gly Val Gly Thr Gly Lys Met Lys
                515                 520                 525
```

-continued

```
tat ctg gag aag gaa ctg gga ata gaa gca ctg caa act atg aag aga       1632
Tyr Leu Glu Lys Glu Leu Gly Ile Glu Ala Leu Gln Thr Met Lys Arg
    530             535                 540 atc aag aaa acg ttg gac cca aac gat atc atg aac ccg gga aag tta       1680
Ile Lys Lys Thr Leu Asp Pro Asn Asp Ile Met Asn Pro Gly Lys Leu
545                 550                 555                 560 att cct cct cat gta tgt ttc taa                                       1704
Ile Pro Pro His Val Cys Phe
                565
```

<210> SEQ ID NO 10
<211> LENGTH: 567
<212> TYPE: PRT
<213> ORGANISM: Arabidopsis thaliana

<400> SEQUENCE: 10

```
Met Ala Phe Ala Ser Lys Phe Ala Arg Ser Lys Thr Ile Leu Ser Phe
1               5                   10                  15

Leu Arg Pro Cys Arg Gln Leu His Ser Thr Pro Lys Ser Thr Gly Asp
                20                  25                  30

Val Thr Val Leu Ser Pro Val Lys Gly Arg Arg Leu Pro Thr Cys
            35                  40                  45

Trp Ser Ser Leu Phe Pro Leu Ala Ile Ala Ala Ser Ala Thr Ser
    50                  55                  60

Phe Ala Tyr Leu Asn Leu Ser Asn Pro Ser Ile Ser Glu Ser Ser
65                  70                  75                  80

Ala Leu Asp Ser Arg Asp Ile Thr Val Gly Gly Lys Asp Ser Thr Glu
                85                  90                  95

Ala Val Val Lys Gly Glu Tyr Lys Gln Val Pro Lys Glu Leu Ile Ser
            100                 105                 110

Gln Leu Lys Thr Ile Leu Glu Asp Asn Leu Thr Thr Asp Tyr Asp Glu
        115                 120                 125

Arg Tyr Phe His Gly Lys Pro Gln Asn Ser Phe His Lys Ala Val Asn
    130                 135                 140

Ile Pro Asp Val Val Phe Pro Arg Ser Glu Glu Val Ser Lys
145                 150                 155                 160

Ile Leu Lys Ser Cys Asn Glu Tyr Lys Val Pro Ile Pro Tyr Gly
                165                 170                 175

Gly Ala Thr Ser Ile Glu Gly His Thr Leu Ala Pro Lys Gly Gly Val
            180                 185                 190

Cys Ile Asp Met Ser Leu Met Lys Arg Val Lys Ala Leu His Val Glu
        195                 200                 205

Asp Met Asp Val Ile Val Glu Pro Gly Ile Gly Trp Leu Glu Leu Asn
    210                 215                 220

Glu Tyr Leu Glu Glu Tyr Gly Leu Phe Phe Pro Leu Asp Pro Gly Pro
225                 230                 235                 240

Gly Ala Ser Ile Gly Gly Met Cys Ala Thr Arg Cys Ser Gly Ser Leu
                245                 250                 255

Ala Val Arg Tyr Gly Thr Met Arg Asp Asn Val Ile Ser Leu Lys Val
            260                 265                 270

Val Leu Pro Asn Gly Asp Val Val Lys Thr Ala Ser Arg Ala Arg Lys
        275                 280                 285

Ser Ala Ala Gly Tyr Asp Leu Thr Arg Leu Ile Ile Gly Ser Glu Gly
    290                 295                 300

Thr Leu Gly Val Ile Thr Glu Ile Thr Leu Arg Leu Gln Lys Ile Pro
305                 310                 315                 320
```

-continued

```
Gln His Ser Val Val Ala Val Cys Asn Phe Pro Thr Val Lys Asp Ala
                325                 330                 335

Ala Asp Val Ala Ile Ala Thr Met Met Ser Gly Ile Gln Val Ser Arg
            340                 345                 350

Val Glu Leu Leu Asp Glu Val Gln Ile Arg Ala Ile Asn Met Ala Asn
        355                 360                 365

Gly Lys Asn Leu Thr Glu Ala Pro Thr Leu Met Phe Glu Phe Ile Gly
    370                 375                 380

Thr Glu Ala Tyr Thr Arg Glu Gln Thr Gln Ile Val Gln Gln Ile Ala
385                 390                 395                 400

Ser Lys His Asn Gly Ser Asp Phe Met Phe Ala Glu Pro Glu Ala
                405                 410                 415

Lys Lys Glu Leu Trp Lys Ile Arg Lys Glu Ala Leu Trp Ala Cys Tyr
            420                 425                 430

Ala Met Ala Pro Gly His Glu Ala Met Ile Thr Asp Val Cys Val Pro
        435                 440                 445

Leu Ser His Leu Ala Glu Leu Ile Ser Arg Ser Lys Lys Glu Leu Asp
    450                 455                 460

Ala Ser Ser Leu Leu Cys Thr Val Ile Ala His Ala Gly Asp Gly Asn
465                 470                 475                 480

Phe His Thr Cys Ile Met Phe Asp Pro Ser Glu Glu Gln Arg Arg
                485                 490                 495

Glu Ala Glu Arg Leu Asn His Phe Met Val His Ser Ala Leu Ser Met
            500                 505                 510

Asp Gly Thr Cys Thr Gly Glu His Gly Val Gly Thr Gly Lys Met Lys
        515                 520                 525

Tyr Leu Glu Lys Glu Leu Gly Ile Glu Ala Leu Gln Thr Met Lys Arg
    530                 535                 540

Ile Lys Lys Thr Leu Asp Pro Asn Asp Ile Met Asn Pro Gly Lys Leu
545                 550                 555                 560

Ile Pro Pro His Val Cys Phe
                565

<210> SEQ ID NO 11
<211> LENGTH: 1782
<212> TYPE: DNA
<213> ORGANISM: Escherichia coli
<220> FEATURE:
<221> NAME/KEY: CDS
<222> LOCATION: (1)..(1779)
<223> OTHER INFORMATION: Glyoxylate Carboligase

<400> SEQUENCE: 11 atg gca aaa atg aga gcc gtt gac gcg gca atg tat gtg ctg gag aaa      48
Met Ala Lys Met Arg Ala Val Asp Ala Ala Met Tyr Val Leu Glu Lys
1               5                   10                  15 gaa ggt atc act acc gcc ttc ggt gtt ccg gga gct gca atc aat ccg      96
Glu Gly Ile Thr Thr Ala Phe Gly Val Pro Gly Ala Ala Ile Asn Pro
            20                  25                  30 ttc tac tca gcg atg cgt aag cac ggc ggt att cgt cac att ctg gcg    144
Phe Tyr Ser Ala Met Arg Lys His Gly Gly Ile Arg His Ile Leu Ala
        35                  40                  45 cgt cat gtg gaa ggt gct tcg cac atg gcg gaa ggt tat acc cgc gca    192
Arg His Val Glu Gly Ala Ser His Met Ala Glu Gly Tyr Thr Arg Ala
    50                  55                  60 acg gca ggg aat atc ggc gta tgt ctg ggg act tcc ggt cct gcg ggc    240
Thr Ala Gly Asn Ile Gly Val Cys Leu Gly Thr Ser Gly Pro Ala Gly
```

-continued

```
                65                  70                  75                  80
acg gac atg atc acc gcg ctc tat tcc gct tct gct gat tcc att cct       288
Thr Asp Met Ile Thr Ala Leu Tyr Ser Ala Ser Ala Asp Ser Ile Pro
                    85                  90                  95 att ctg tgc att acc ggc cag gca ccg cgc gcc cgt ctg cat aaa gaa       336
Ile Leu Cys Ile Thr Gly Gln Ala Pro Arg Ala Arg Leu His Lys Glu
                100                 105                 110 gat ttt cag gcc gta gat att gaa gca att gct aaa ccg gtc agc aaa       384
Asp Phe Gln Ala Val Asp Ile Glu Ala Ile Ala Lys Pro Val Ser Lys
            115                 120                 125 atg gcg gtt aca gtt cgt gaa gcg gcg ctg gtg cct cgc gtg ctg caa       432
Met Ala Val Thr Val Arg Glu Ala Ala Leu Val Pro Arg Val Leu Gln
    130                 135                 140 cag gca ttt cac ctg atg cgt tct ggt cgt ccg ggt ccg gta ctg gtg       480
Gln Ala Phe His Leu Met Arg Ser Gly Arg Pro Gly Pro Val Leu Val
145                 150                 155                 160 gat tta ccg ttc gac gtt cag gtt gcg gaa atc gag ttt gat cct gac       528
Asp Leu Pro Phe Asp Val Gln Val Ala Glu Ile Glu Phe Asp Pro Asp
                165                 170                 175 atg tac gaa ccg ctg ccg gtc tac aaa cct gct gcc agc cgt atg cag       576
Met Tyr Glu Pro Leu Pro Val Tyr Lys Pro Ala Ala Ser Arg Met Gln
            180                 185                 190 atc gaa aaa gct gta gaa atg tta atc cag gcc gaa cgt ccg gtg att       624
Ile Glu Lys Ala Val Glu Met Leu Ile Gln Ala Glu Arg Pro Val Ile
        195                 200                 205 gtt gcc ggg ggc ggg gta att aat gct gac gca gct gca ctg tta caa       672
Val Ala Gly Gly Gly Val Ile Asn Ala Asp Ala Ala Ala Leu Leu Gln
    210                 215                 220 cag ttt gct gaa ctg acc agc gtt ccg gtg atc cca acg cta atg ggc       720
Gln Phe Ala Glu Leu Thr Ser Val Pro Val Ile Pro Thr Leu Met Gly
225                 230                 235                 240 tgg ggc tgt atc ccg gac gat cat gaa ctg atg gcc ggg atg gtg ggt       768
Trp Gly Cys Ile Pro Asp Asp His Glu Leu Met Ala Gly Met Val Gly
                245                 250                 255 ctg caa acc gcg cat cgt tac ggt aac gca acg ctg ctg gcg tct gac       816
Leu Gln Thr Ala His Arg Tyr Gly Asn Ala Thr Leu Leu Ala Ser Asp
            260                 265                 270 atg gtg ttt ggt atc ggt aac cgt ttt gct aac cgt cat acc ggc tcg       864
Met Val Phe Gly Ile Gly Asn Arg Phe Ala Asn Arg His Thr Gly Ser
        275                 280                 285 gta gag aaa tac acc gaa ggg cgc aaa atc gtt cat att gat att gag       912
Val Glu Lys Tyr Thr Glu Gly Arg Lys Ile Val His Ile Asp Ile Glu
    290                 295                 300 ccg acg caa att ggt cgc gtg ctg tgt ccg gat ctc ggt att gtc tct       960
Pro Thr Gln Ile Gly Arg Val Leu Cys Pro Asp Leu Gly Ile Val Ser
305                 310                 315                 320 gat gct aaa gcg gcg ctg aca ctg ctg gtt gaa gtg gcg cag gag atg      1008
Asp Ala Lys Ala Ala Leu Thr Leu Leu Val Glu Val Ala Gln Glu Met
                325                 330                 335 caa aaa gcg ggt cgt ctg ccg tgt cgt aaa gaa tgg gtc gcc gac tgc      1056
Gln Lys Ala Gly Arg Leu Pro Cys Arg Lys Glu Trp Val Ala Asp Cys
            340                 345                 350 cag cag cgt aaa cgc act ttg ctg cgc aaa acc cac ttc gac aac gtg      1104
Gln Gln Arg Lys Arg Thr Leu Leu Arg Lys Thr His Phe Asp Asn Val
        355                 360                 365 ccg gtg aaa ccg cag cgc gtg tat gaa gag atg aac aaa gcc ttt ggt      1152
Pro Val Lys Pro Gln Arg Val Tyr Glu Glu Met Asn Lys Ala Phe Gly
    370                 375                 380 cgc gat gtt tgt tat gtc acc acc att ggt ctg tca caa atc gct gcg      1200
Arg Asp Val Cys Tyr Val Thr Thr Ile Gly Leu Ser Gln Ile Ala Ala
```

-continued

```
Arg Asp Val Cys Tyr Val Thr Thr Ile Gly Leu Ser Gln Ile Ala Ala
385                 390                 395                 400 gca caa atg ctg cat gtc ttt aaa gac cgc cac tgg atc aac tgt ggt      1248
Ala Gln Met Leu His Val Phe Lys Asp Arg His Trp Ile Asn Cys Gly
            405                 410                 415 cag gct ggt ccg tta ggc tgg acg att ccg gct gcg cta ggg gtt tgt      1296
Gln Ala Gly Pro Leu Gly Trp Thr Ile Pro Ala Ala Leu Gly Val Cys
        420                 425                 430 gcc gct gat ccg aaa cgc aat gtg gtg gcg att tct ggc gac ttt gac      1344
Ala Ala Asp Pro Lys Arg Asn Val Val Ala Ile Ser Gly Asp Phe Asp
    435                 440                 445 ttc cag ttc ctg att gaa gag tta gct gtt ggc gcg cag ttc aac att      1392
Phe Gln Phe Leu Ile Glu Glu Leu Ala Val Gly Ala Gln Phe Asn Ile
450                 455                 460 ccg tac atc cat gtg ctg gtc aac aac gct tat ctg ggg ctg att cgt      1440
Pro Tyr Ile His Val Leu Val Asn Asn Ala Tyr Leu Gly Leu Ile Arg
465                 470                 475                 480 cag tca caa cgc gct ttt gac atg gac tac tgc gtg caa ctc gct ttc      1488
Gln Ser Gln Arg Ala Phe Asp Met Asp Tyr Cys Val Gln Leu Ala Phe
            485                 490                 495 gag aat atc aac tcc agt gaa gtg aat ggc tac ggt gtt gac cac gta      1536
Glu Asn Ile Asn Ser Ser Glu Val Asn Gly Tyr Gly Val Asp His Val
        500                 505                 510 aaa gta gcg gaa ggt tta ggt tgt aaa gct att cgg gtc ttc aaa ccg      1584
Lys Val Ala Glu Gly Leu Gly Cys Lys Ala Ile Arg Val Phe Lys Pro
    515                 520                 525 gaa gat att gcg cca gcc ttt gaa cag gcg aaa gcc tta atg gcg caa      1632
Glu Asp Ile Ala Pro Ala Phe Glu Gln Ala Lys Ala Leu Met Ala Gln
530                 535                 540 tat cgg gta ccg gta gtc gtg gaa gtt att ctc gag cgt gtg acc aat      1680
Tyr Arg Val Pro Val Val Val Glu Val Ile Leu Glu Arg Val Thr Asn
545                 550                 555                 560 att tcg atg ggc agc gaa ctg gat aac gtc atg gaa ttt gaa gat atc      1728
Ile Ser Met Gly Ser Glu Leu Asp Asn Val Met Glu Phe Glu Asp Ile
            565                 570                 575 gcc gat aac gca gcg gac gca ccg act gaa acc tgc ttc atg cac tat      1776
Ala Asp Asn Ala Ala Asp Ala Pro Thr Glu Thr Cys Phe Met His Tyr
        580                 585                 590 gaa taa                                                              1782
Glu
```

<210> SEQ ID NO 12
<211> LENGTH: 593
<212> TYPE: PRT
<213> ORGANISM: Escherichia coli

<400> SEQUENCE: 12

```
Met Ala Lys Met Arg Ala Val Asp Ala Ala Met Tyr Val Leu Glu Lys
1               5                   10                  15

Glu Gly Ile Thr Thr Ala Phe Gly Val Pro Gly Ala Ala Ile Asn Pro
            20                  25                  30

Phe Tyr Ser Ala Met Arg Lys His Gly Gly Ile Arg His Ile Leu Ala
        35                  40                  45

Arg His Val Glu Gly Ala Ser His Met Ala Glu Gly Tyr Thr Arg Ala
    50                  55                  60

Thr Ala Gly Asn Ile Gly Val Cys Leu Gly Thr Ser Gly Pro Ala Gly
65                  70                  75                  80

Thr Asp Met Ile Thr Ala Leu Tyr Ser Ala Ser Ala Asp Ser Ile Pro
            85                  90                  95
```

-continued

Ile Leu Cys Ile Thr Gly Gln Ala Pro Arg Ala Arg Leu His Lys Glu
            100                 105                 110

Asp Phe Gln Ala Val Asp Ile Glu Ala Ile Ala Lys Pro Val Ser Lys
        115                 120                 125

Met Ala Val Thr Val Arg Glu Ala Ala Leu Val Pro Arg Val Leu Gln
    130                 135                 140

Gln Ala Phe His Leu Met Arg Ser Gly Arg Pro Gly Pro Val Leu Val
145                 150                 155                 160

Asp Leu Pro Phe Asp Val Gln Val Ala Glu Ile Glu Phe Asp Pro Asp
                165                 170                 175

Met Tyr Glu Pro Leu Pro Val Tyr Lys Pro Ala Ala Ser Arg Met Gln
            180                 185                 190

Ile Glu Lys Ala Val Glu Met Leu Ile Gln Ala Glu Arg Pro Val Ile
        195                 200                 205

Val Ala Gly Gly Gly Val Ile Asn Ala Asp Ala Ala Leu Leu Gln
    210                 215                 220

Gln Phe Ala Glu Leu Thr Ser Val Pro Val Ile Pro Thr Leu Met Gly
225                 230                 235                 240

Trp Gly Cys Ile Pro Asp Asp His Glu Leu Met Ala Gly Met Val Gly
                245                 250                 255

Leu Gln Thr Ala His Arg Tyr Gly Asn Ala Thr Leu Leu Ala Ser Asp
            260                 265                 270

Met Val Phe Gly Ile Gly Asn Arg Phe Ala Asn Arg His Thr Gly Ser
        275                 280                 285

Val Glu Lys Tyr Thr Glu Gly Arg Lys Ile Val His Ile Asp Ile Glu
    290                 295                 300

Pro Thr Gln Ile Gly Arg Val Leu Cys Pro Asp Leu Gly Ile Val Ser
305                 310                 315                 320

Asp Ala Lys Ala Ala Leu Thr Leu Leu Val Glu Val Ala Gln Glu Met
                325                 330                 335

Gln Lys Ala Gly Arg Leu Pro Cys Arg Lys Glu Trp Val Ala Asp Cys
            340                 345                 350

Gln Gln Arg Lys Arg Thr Leu Leu Arg Lys Thr His Phe Asp Asn Val
        355                 360                 365

Pro Val Lys Pro Gln Arg Val Tyr Glu Glu Met Asn Lys Ala Phe Gly
    370                 375                 380

Arg Asp Val Cys Tyr Val Thr Thr Ile Gly Leu Ser Gln Ile Ala Ala
385                 390                 395                 400

Ala Gln Met Leu His Val Phe Lys Asp Arg His Trp Ile Asn Cys Gly
                405                 410                 415

Gln Ala Gly Pro Leu Gly Trp Thr Ile Pro Ala Ala Leu Gly Val Cys
            420                 425                 430

Ala Ala Asp Pro Lys Arg Asn Val Val Ala Ile Ser Gly Asp Phe Asp
        435                 440                 445

Phe Gln Phe Leu Ile Glu Glu Leu Ala Val Gly Ala Gln Phe Asn Ile
    450                 455                 460

Pro Tyr Ile His Val Leu Val Asn Asn Ala Tyr Leu Gly Leu Ile Arg
465                 470                 475                 480

Gln Ser Gln Arg Ala Phe Asp Met Asp Tyr Cys Val Gln Leu Ala Phe
                485                 490                 495

Glu Asn Ile Asn Ser Ser Glu Val Asn Gly Tyr Gly Val Asp His Val
            500                 505                 510

-continued

```
Lys Val Ala Glu Gly Leu Gly Cys Lys Ala Ile Arg Val Phe Lys Pro
            515                 520                 525

Glu Asp Ile Ala Pro Ala Phe Glu Gln Ala Lys Ala Leu Met Ala Gln
    530                 535                 540

Tyr Arg Val Pro Val Val Glu Val Ile Leu Glu Arg Val Thr Asn
545                 550                 555                 560

Ile Ser Met Gly Ser Glu Leu Asp Asn Val Met Glu Phe Glu Asp Ile
                565                 570                 575

Ala Asp Asn Ala Ala Asp Ala Pro Thr Glu Thr Cys Phe Met His Tyr
            580                 585                 590

Glu
```

<210> SEQ ID NO 13
<211> LENGTH: 879
<212> TYPE: DNA
<213> ORGANISM: Escherichia coli
<220> FEATURE:
<221> NAME/KEY: CDS
<222> LOCATION: (1)..(876)
<223> OTHER INFORMATION: Tartronic Semialdehyde Reductase

<400> SEQUENCE: 13

```
atg aaa ctg gga ttt att ggc tta ggc att atg ggt aca ccg atg gcc        48
Met Lys Leu Gly Phe Ile Gly Leu Gly Ile Met Gly Thr Pro Met Ala
1               5                   10                  15 att aat ctg gcg cgt gcc ggt cat caa tta cat gtc acg acc att gga        96
Ile Asn Leu Ala Arg Ala Gly His Gln Leu His Val Thr Thr Ile Gly
            20                  25                  30 ccg gtt gct gat gaa tta ctg tca ctg ggt gcc gtc agt gtt gaa act       144
Pro Val Ala Asp Glu Leu Leu Ser Leu Gly Ala Val Ser Val Glu Thr
        35                  40                  45 gct cgc cag gta acg gaa gca tcg gac atc att ttt att atg gtg ccg       192
Ala Arg Gln Val Thr Glu Ala Ser Asp Ile Ile Phe Ile Met Val Pro
    50                  55                  60 gac aca cct cag gtt gaa gaa gtt ctg ttc ggt gaa aat ggt tgt acc       240
Asp Thr Pro Gln Val Glu Glu Val Leu Phe Gly Glu Asn Gly Cys Thr
65                  70                  75                  80 aaa gcc tcg ctg aag ggc aaa acc att gtt gat atg agc tcc att tcc       288
Lys Ala Ser Leu Lys Gly Lys Thr Ile Val Asp Met Ser Ser Ile Ser
                85                  90                  95 ccg att gaa act aag cgt ttc gct cgt cag gtg aat gaa ctg ggc ggc       336
Pro Ile Glu Thr Lys Arg Phe Ala Arg Gln Val Asn Glu Leu Gly Gly
            100                 105                 110 gat tat ctc gat gcg cca gtc tcc ggc ggt gaa atc ggt gcg cgt gaa       384
Asp Tyr Leu Asp Ala Pro Val Ser Gly Gly Glu Ile Gly Ala Arg Glu
        115                 120                 125 ggg acg ttg tcg att atg gtt ggc ggt gat gaa gcg gta ttt gaa cgt       432
Gly Thr Leu Ser Ile Met Val Gly Gly Asp Glu Ala Val Phe Glu Arg
    130                 135                 140 gtt aaa ccg ctg ttt gaa ctg ctc ggt aaa aat atc acc ctc gtg ggc       480
Val Lys Pro Leu Phe Glu Leu Leu Gly Lys Asn Ile Thr Leu Val Gly
145                 150                 155                 160 ggt aac ggc gat ggt caa acc tgc aaa gtg gca aat cag att atc gtg       528
Gly Asn Gly Asp Gly Gln Thr Cys Lys Val Ala Asn Gln Ile Ile Val
                165                 170                 175 gcg ctc aat att gaa gcg gtt tct gaa gcc ctg cta ttt gct tca aaa       576
Ala Leu Asn Ile Glu Ala Val Ser Glu Ala Leu Leu Phe Ala Ser Lys
            180                 185                 190 gcc ggt gcg gac ccg gta cgt gtg cgc cag gcg ctg atg ggc ggc ttt       624
Ala Gly Ala Asp Pro Val Arg Val Arg Gln Ala Leu Met Gly Gly Phe
```

```
gct tcc tca cgt att ctg gaa gtt cat ggc gag cgt atg att aaa cgc    672
Ala Ser Ser Arg Ile Leu Glu Val His Gly Glu Arg Met Ile Lys Arg
    210             215                 220 acc ttt aat ccg ggc ttc aaa atc gct ctg cac cag aaa gat ctc aac    720
Thr Phe Asn Pro Gly Phe Lys Ile Ala Leu His Gln Lys Asp Leu Asn
225                 230                 235                 240 ctg gca ctg caa agt gcg aaa gca ctt gcg ctg aac ctg cca aac act    768
Leu Ala Leu Gln Ser Ala Lys Ala Leu Ala Leu Asn Leu Pro Asn Thr
                245                 250                 255 gcg acc tgc cag gag tta ttt aat acc tgt gcg gca aac ggt ggc agc    816
Ala Thr Cys Gln Glu Leu Phe Asn Thr Cys Ala Ala Asn Gly Gly Ser
            260                 265                 270 cag ttg gat cac tct gcg tta gtg cag gcg ctg gaa tta atg gct aac    864
Gln Leu Asp His Ser Ala Leu Val Gln Ala Leu Glu Leu Met Ala Asn
        275                 280                 285 cat aaa ctg gcc tga                                                 879
His Lys Leu Ala
    290

<210> SEQ ID NO 14
<211> LENGTH: 292
<212> TYPE: PRT
<213> ORGANISM: Escherichia coli

<400> SEQUENCE: 14

Met Lys Leu Gly Phe Ile Gly Leu Gly Ile Met Gly Thr Pro Met Ala
1               5                   10                  15

Ile Asn Leu Ala Arg Ala Gly His Gln Leu His Val Thr Thr Ile Gly
            20                  25                  30

Pro Val Ala Asp Glu Leu Leu Ser Leu Gly Ala Val Ser Val Glu Thr
        35                  40                  45

Ala Arg Gln Val Thr Glu Ala Ser Asp Ile Ile Phe Ile Met Val Pro
    50                  55                  60

Asp Thr Pro Gln Val Glu Glu Val Leu Phe Gly Glu Asn Gly Cys Thr
65                  70                  75                  80

Lys Ala Ser Leu Lys Gly Lys Thr Ile Val Asp Met Ser Ser Ile Ser
                85                  90                  95

Pro Ile Glu Thr Lys Arg Phe Ala Arg Gln Val Asn Glu Leu Gly Gly
            100                 105                 110

Asp Tyr Leu Asp Ala Pro Val Ser Gly Gly Glu Ile Gly Ala Arg Glu
        115                 120                 125

Gly Thr Leu Ser Ile Met Val Gly Gly Asp Glu Ala Val Phe Glu Arg
    130                 135                 140

Val Lys Pro Leu Phe Glu Leu Leu Gly Lys Asn Ile Thr Leu Val Gly
145                 150                 155                 160

Gly Asn Gly Asp Gly Gln Thr Cys Lys Val Ala Asn Gln Ile Ile Val
                165                 170                 175

Ala Leu Asn Ile Glu Ala Val Ser Glu Ala Leu Leu Phe Ala Ser Lys
            180                 185                 190

Ala Gly Ala Asp Pro Val Arg Val Arg Gln Ala Leu Met Gly Gly Phe
        195                 200                 205

Ala Ser Ser Arg Ile Leu Glu Val His Gly Glu Arg Met Ile Lys Arg
    210                 215                 220

Thr Phe Asn Pro Gly Phe Lys Ile Ala Leu His Gln Lys Asp Leu Asn
225                 230                 235                 240
```

-continued

```
Leu Ala Leu Gln Ser Ala Lys Ala Leu Ala Leu Asn Leu Pro Asn Thr
            245                 250                 255

Ala Thr Cys Gln Glu Leu Phe Asn Thr Cys Ala Ala Asn Gly Gly Ser
            260                 265                 270

Gln Leu Asp His Ser Ala Leu Val Gln Ala Leu Glu Leu Met Ala Asn
            275                 280                 285

His Lys Leu Ala
    290
```